(12) United States Patent
Kiani

(10) Patent No.: US 11,866,782 B2
(45) Date of Patent: Jan. 9, 2024

(54) MULTI-OMIC ANALYSIS IN MONODISPERSE DROPLETS

(71) Applicant: Fluent Biosciences Inc., Watertown, MA (US)

(72) Inventor: Sepehr Kiani, Watertown, MA (US)

(73) Assignee: Fluent Biosciences Inc., Watertown, MA (US)

( * ) Notice: Subject to any disclaimer, the term of this patent is extended or adjusted under 35 U.S.C. 154(b) by 276 days.

(21) Appl. No.: 17/202,783

(22) Filed: Mar. 16, 2021

(65) Prior Publication Data

US 2021/0332432 A1    Oct. 28, 2021

Related U.S. Application Data

(60) Provisional application No. 62/990,368, filed on Mar. 16, 2020.

(51) Int. Cl.
  *C12Q 1/6876* (2018.01)
  *C12N 15/10* (2006.01)
  *C12Q 1/686* (2018.01)

(52) U.S. Cl.
  CPC ....... *C12Q 1/6876* (2013.01); *C12N 15/1096* (2013.01); *C12Q 1/686* (2013.01)

(58) Field of Classification Search
  None
  See application file for complete search history.

(56) References Cited

U.S. PATENT DOCUMENTS

| 4,701,415 A | 10/1987 | Dutton |
| 5,512,439 A | 4/1996 | Hornes et al. |
| 5,813,759 A | 9/1998 | Gebrian |
| 6,210,891 B1 | 4/2001 | Nyren et al. |
| 6,306,597 B1 | 10/2001 | Macevicz |
| 6,309,833 B1 | 10/2001 | Edman et al. |
| 6,828,100 B1 | 12/2004 | Ronaghi |
| 6,833,246 B2 | 12/2004 | Balasubramanian |

(Continued)

FOREIGN PATENT DOCUMENTS

| AU | 2013203624 A1 | 5/2013 |
| EP | 3819637 A1 | 5/2021 |

(Continued)

OTHER PUBLICATIONS

Peterson, V. et al., Multiplexed quantification of proteins and transcripts in single cells, Nature Biotechnol., vol. 35, pp. 936-939 plus online methods pp. 1-3 (Year: 2017).*

(Continued)

*Primary Examiner* — Teresa E Strzelecka
(74) *Attorney, Agent, or Firm* — Withers Bergman LLP; Thomas C. Meyers

(57) ABSTRACT

This disclosure provides methods and systems for single-cell, multi-omic analysis of target cells without microfluidic devices. The disclosed methods involve the use of template particles to template the formation of monodisperse droplets to generally capture a single target cell from a population of cells in an encapsulation, derive a plurality of distinct mRNA molecules from the single target cell, and quantify the distinct mRNA molecules to generate an expression profile. Nucleic-acid-tagged antibody conjugates are used for simultaneous proteomic analysis along with the gene expression profiling.

19 Claims, 6 Drawing Sheets

Specification includes a Sequence Listing.

(56) References Cited

U.S. PATENT DOCUMENTS

| | | |
|---|---|---|
| 6,911,345 B2 | 6/2005 | Quake et al. |
| 7,232,656 B2 | 6/2007 | Balasubramanian et al. |
| 7,537,897 B2 | 5/2009 | Brenner et al. |
| 7,598,035 B2 | 10/2009 | Macevicz |
| 7,835,871 B2 | 11/2010 | Kain et al. |
| 7,842,457 B2 | 11/2010 | Berka et al. |
| 7,960,120 B2 | 6/2011 | Rigatti et al. |
| 8,012,690 B2 | 9/2011 | Berka et al. |
| 8,629,323 B2 | 1/2014 | Weeks |
| 8,715,934 B2 | 5/2014 | Diehl et al. |
| 8,748,102 B2 | 6/2014 | Berka et al. |
| 8,765,380 B2 | 7/2014 | Berka et al. |
| 9,011,777 B2 | 4/2015 | Beer |
| 9,012,390 B2 | 4/2015 | Holtze et al. |
| 9,085,798 B2 | 7/2015 | Chee |
| 9,260,751 B2 | 2/2016 | Diehl et al. |
| 9,388,465 B2 | 7/2016 | Hindson et al. |
| 9,399,797 B2 | 7/2016 | Hutchison et al. |
| 9,562,837 B2 | 2/2017 | Link |
| 9,567,645 B2 | 2/2017 | Fan et al. |
| 9,567,646 B2 | 2/2017 | Fan et al. |
| 9,580,736 B2 | 2/2017 | Tan et al. |
| 9,598,736 B2 | 3/2017 | Fan et al. |
| 9,637,799 B2 | 5/2017 | Fan et al. |
| 9,650,629 B2 | 5/2017 | Froehlich et al. |
| 9,695,474 B2 | 7/2017 | Johnson et al. |
| 9,701,998 B2 | 7/2017 | Hindson et al. |
| 9,708,654 B2 | 7/2017 | Hunicke-Smith et al. |
| 9,783,847 B2 | 10/2017 | Chee |
| 9,951,386 B2 | 4/2018 | Hindson et al. |
| 10,030,267 B2 | 7/2018 | Hindson et al. |
| 10,041,116 B2 | 8/2018 | Hindson et al. |
| 10,131,958 B1 | 11/2018 | Fan et al. |
| 10,151,003 B2 | 12/2018 | Fan et al. |
| 10,155,981 B2 | 12/2018 | Brenner et al. |
| 10,202,628 B2 | 2/2019 | Church et al. |
| 10,208,356 B1 | 2/2019 | Fan et al. |
| 10,221,442 B2 | 3/2019 | Hindson et al. |
| 10,240,192 B2 | 3/2019 | Berka et al. |
| 10,240,197 B1 | 3/2019 | Brenner et al. |
| 10,253,375 B1 | 4/2019 | Fan et al. |
| 10,266,883 B2 | 4/2019 | Chee |
| 10,280,459 B1 | 5/2019 | Brenner et al. |
| 10,285,940 B2 | 5/2019 | Mason et al. |
| 10,329,557 B2 | 6/2019 | Johnson et al. |
| 10,344,329 B2 | 7/2019 | Hindson et al. |
| 10,392,662 B1 | 8/2019 | Brenner et al. |
| 10,400,280 B2 | 9/2019 | Hindson et al. |
| 10,415,030 B2 | 9/2019 | Marshall et al. |
| 10,457,986 B2 | 10/2019 | Hindson et al. |
| 10,501,793 B2 | 12/2019 | Chee |
| 10,584,381 B2 | 3/2020 | Hindson et al. |
| 11,060,149 B2 | 7/2021 | Steelman |
| 11,104,961 B2 | 8/2021 | Fontanez et al. |
| 11,142,791 B2 | 10/2021 | Abate et al. |
| 2002/0132251 A1 | 9/2002 | Shuber |
| 2003/0143599 A1 | 7/2003 | Makarov et al. |
| 2003/0180737 A1 | 9/2003 | Gu et al. |
| 2004/0005585 A1 | 1/2004 | Bi et al. |
| 2006/0024681 A1 | 2/2006 | Smith et al. |
| 2006/0177836 A1 | 8/2006 | McKernan et al. |
| 2006/0292611 A1 | 12/2006 | Berka et al. |
| 2007/0080316 A1 | 4/2007 | Sauer et al. |
| 2007/0114362 A1 | 5/2007 | Feng et al. |
| 2008/0004436 A1 | 1/2008 | Tawfik |
| 2009/0280475 A1 | 11/2009 | Pollack et al. |
| 2011/0009278 A1 | 1/2011 | Kain et al. |
| 2011/0086780 A1 | 4/2011 | Colston, Jr. et al. |
| 2011/0118151 A1 | 5/2011 | Eshoo et al. |
| 2011/0311978 A1 | 12/2011 | Makarewicz, Jr. et al. |
| 2012/0295269 A1 | 11/2012 | Pourahmadi et al. |
| 2012/0316074 A1 | 12/2012 | Saxonov |
| 2013/0115169 A1 | 5/2013 | Lahann et al. |
| 2014/0155295 A1 | 6/2014 | Hindson et al. |
| 2015/0133312 A1 | 5/2015 | Bielas et al. |
| 2015/0225777 A1 | 8/2015 | Hindson et al. |
| 2016/0186267 A1 | 6/2016 | So et al. |
| 2016/0250608 A1 | 9/2016 | Anders et al. |
| 2016/0274103 A1 | 9/2016 | Piloto et al. |
| 2017/0192030 A1 | 7/2017 | Lapham et al. |
| 2017/0218437 A1 | 8/2017 | Seul et al. |
| 2017/0232417 A1 | 8/2017 | Lebofsky et al. |
| 2017/0255160 A1 | 9/2017 | Numata et al. |
| 2018/0010105 A1 | 1/2018 | Rogers et al. |
| 2018/0051321 A1 | 2/2018 | Hindson et al. |
| 2018/0119216 A1 | 5/2018 | Jamshidi et al. |
| 2018/0133715 A1 | 5/2018 | Craig et al. |
| 2018/0179553 A1 | 6/2018 | Watson et al. |
| 2018/0216162 A1 | 8/2018 | Belhocine et al. |
| 2018/0237836 A1 | 8/2018 | Abate et al. |
| 2018/0274027 A1 | 9/2018 | Hindson et al. |
| 2018/0355407 A1 | 12/2018 | Utharala et al. |
| 2019/0085412 A1 | 3/2019 | Fan et al. |
| 2019/0153532 A1 | 5/2019 | Bharadwaj et al. |
| 2019/0153550 A1 | 5/2019 | Steinmetzer et al. |
| 2019/0177789 A1 | 6/2019 | Hindson et al. |
| 2019/0323003 A1 | 10/2019 | Ramji et al. |
| 2019/0323091 A1 | 10/2019 | Bramlett et al. |
| 2019/0352714 A1 | 11/2019 | Salk et al. |
| 2019/0381497 A1 | 12/2019 | Di Carlo et al. |
| 2019/0382753 A1 | 12/2019 | Steemers et al. |
| 2020/0040385 A1 | 2/2020 | Beechem et al. |
| 2020/0080112 A1 | 3/2020 | Zhang et al. |
| 2020/0190513 A1 | 6/2020 | Fernandez et al. |
| 2020/0261879 A1 | 8/2020 | Abate et al. |
| 2020/0324287 A1 | 10/2020 | Vijayan et al. |
| 2020/0376488 A1 | 12/2020 | Wu et al. |
| 2021/0010070 A1 | 1/2021 | Schnall-Levin et al. |
| 2021/0054369 A1 | 2/2021 | Meltzer et al. |
| 2021/0214721 A1 | 7/2021 | Fontanez et al. |
| 2021/0214763 A1 | 7/2021 | Fontanez et al. |
| 2021/0214769 A1 | 7/2021 | Fontanez et al. |
| 2021/0214792 A1 | 7/2021 | Fontanez et al. |
| 2021/0214802 A1 | 7/2021 | Fontanez et al. |
| 2021/0215591 A1 | 7/2021 | Fontanez et al. |
| 2021/0301354 A1 | 9/2021 | Kiani |
| 2021/0332432 A1 | 10/2021 | Kiani |
| 2021/0340596 A1 | 11/2021 | Meltzer et al. |
| 2021/0381064 A1 | 12/2021 | Fontanez et al. |
| 2022/0017892 A1 | 1/2022 | Meltzer et al. |
| 2022/0135966 A1 | 5/2022 | Meltzer |
| 2022/0136071 A1 | 5/2022 | Meltzer |
| 2022/0154248 A1 | 5/2022 | Abate et al. |
| 2022/0235416 A1 | 7/2022 | Fontanez et al. |
| 2022/0267761 A1 | 8/2022 | Fontanez et al. |

FOREIGN PATENT DOCUMENTS

| | | |
|---|---|---|
| JP | 2021072863 A | 5/2021 |
| WO | 1997/008547 A1 | 3/1997 |
| WO | 2010/117620 A2 | 10/2010 |
| WO | 2011/047307 A1 | 4/2011 |
| WO | 2012/116146 A1 | 8/2012 |
| WO | 2012/149042 A2 | 11/2012 |
| WO | 2013/165748 A1 | 11/2013 |
| WO | 2014/028537 A1 | 2/2014 |
| WO | 2014/100434 A1 | 6/2014 |
| WO | 2014/146025 A1 | 9/2014 |
| WO | 2014/153071 A1 | 9/2014 |
| WO | 2015/157369 A1 | 10/2015 |
| WO | 2015/187792 A1 | 12/2015 |
| WO | 2016/025815 A1 | 2/2016 |
| WO | 2016/040476 A1 | 3/2016 |
| WO | 2016/126871 A2 | 8/2016 |
| WO | 2016/138080 A1 | 9/2016 |
| WO | 2016/172373 A1 | 10/2016 |
| WO | 2017/161306 A1 | 9/2017 |
| WO | 2019/011971 A1 | 1/2019 |
| WO | 2019/023627 A1 | 1/2019 |
| WO | 2019/139650 A2 | 7/2019 |
| WO | 2019/157529 A1 | 8/2019 |
| WO | 2019/204229 A1 | 10/2019 |
| WO | 2019/217552 A1 | 11/2019 |
| WO | 2019/222523 A2 | 11/2019 |

(56) References Cited

FOREIGN PATENT DOCUMENTS

| WO | 20200037214 A1 | 2/2020 |
| WO | 2020/069268 A1 | 4/2020 |
| WO | 2020/069298 A1 | 4/2020 |

OTHER PUBLICATIONS

Peterson, V. et al., Multiplexed quantification of proteins and transcripts in single cells, Nature Biotechnol., vol. 35, pp. 936-939 plus online methods pp. 1-3, supplementary material pp. 1-37 (Year: 2017).*

Hatori, M.N. et al., Particle Templated Emulsification for Microfluidics-Free Digital Biology, Anal. Chem., vol. 90, pp. 9813-9820 (Year: 2016).*

Cheng, 2020, Ultra-senstive and rapid detection of nucleic acids and microorganisms in body fluids using single molecule tethering, Nature Communications, 11(1):1-9.

Jacobsen, 2004, Direct isolation of poly(A)+ RNA from 4 M guanidine thiocyanate-lysed cell extracts using locked nucleic acid-oligo(T) capture, Nucleic Acids Research, 32(7), 10 pages.

Klein, 2015, Droplet barcoding for single cell transcriptomics applied to embryonic stem cells, Cells, 161(5):1187-1201.

Suh, Synthesis of magnetic hydrogel microparticles for bioassays and tweezer manipulation in microwells, Microfluid Nanofluid, 13:655-674.

Berensmeier, 2006, Magnetic particles for the separation and purification of necleic acids, Applied Microbiology and Biotechnology, 73:495-504.

Biocompare, 2013, How to maintain a constant temp in your CO2 incubator, Jan. 17, 2013 (Jan. 17, 2013) [online] retrieved from <URL: https://www.biocompare.com/Editorial-Articles/126328-Incubators/#:~text=A jacket of water circulates, thermal buffer against outside air.> entire document, 7 pages.

Brouzes, 2009, Droplet microfluidic technology for single-cell high-throughput screening, Proc Natl Acad Sci 106(34):14195-14200.

Cai, 2019, Selection of DNA-encoded libraries to protein targets within and on living cells, Journal of the American Chemical Society, 141(43):1-11.

Datlinger, 2017, Pooled CRISPR screening with single-cell transcriptome readout, Nature Methods 4(3):297-301.

High containment laboratories at CDC—Fifty Years of Excellence, Centers for Disease Control and Prevention, retreived from the internet, <https://www.cdc.gov/ncezid/dhcpp/hcl-50/high-containment-laboratories.html>, 1 page.

Kim, 2018, Single-Cell RT-PCR in Microfluidic Droplets with Integrated Chemical Lysis, Anal Chem 90(2):1273-1279.

Kukurba, 2015, RNA Sequencing and Analysis, Cold Spring Harb Protoc 11:951-969.

Markus, 2021, Analysis of recurrently protected genomic regions in cell-free DNA found in urine, Science Translational Medicine, 13(581):1-31.

Patel, 2019, Design and fabrication of low cost vortex mixer using additive manufacturing, International Journal of Applied Engineering Research 14(1):246-249.

Petersen, 2021, Screening of DNA-encoded small molecule libraries inside a living cell, Journal of the American Chemical Society, 143(7):2751-2756.

Quail, 2012, A tale of three next generation sequencing platforms: comparison of Ion Torrent, Pacific Biosciences and Illumina MiSeq sequencers, BMC Genomics 13:341, 13 pages.

Replogle, 2020, Combinatorial single-cell CRISPR screens by direct guide RNA capture and targeted sequencing, Nat. Biotechnol. 38(8):954-961.

Stoeckius, 2017, Large-scale simultaneous measurements of epitopes and transcriptomes in single cells, Nat Methods 14(9):865-868.

Tokunaga, 2013, Systematic exploration of lipophilic tags that allow efficient anchoring of aptamers to live cell surfaces, Chem Lett 42(2):127-129.

Hatori, 2019, Particle-Templated Emulsification for Microfluidics-Free Digital Biology, Analytical Chemistry, 90:9813-9820.

International Search Report and Written Opinion issued in International Application No. PCT/US2020/47214, dated Feb. 2, 2021, 14 pages.

International Search Report and Written Opinion issued in International Application No. PCT/US2021/013042, dated Mar. 29, 2021, 9 pages.

International Search Report and Written Opinion issued in International Application No. PCT/US2021/013045, dated Mar. 29, 2021, 8 pages.

International Search Report and Written Opinion issued in International Application No. PCT/US2021/013065, dated Mar. 29, 2021, 11 pages.

International Search Report and Written Opinion issued in International Application No. PCT/US2021/013066, dated Mar. 29, 2021, 11 pages.

International Search Report and Written Opinion issued in International Application No. PCT/US2021/13048, dated Mar. 31, 2021, 20 pages.

International Search Report and Written Opinion issued in International Application No. PCT/US2021/13069, dated Apr. 1, 2021, 14 pages.

Kumari, 2017, Quantification of Circulating Free DNA as a Diagnostic Marker in Gall Bladder Cancer, Pathology & Oncology Research, 23:91-97.

Mazutis, 2013, Singl-cell analysis and sorting using droplet-based microfluidics, Nature Protocols, 8(5):870-891.

Non-Final Office Action issued in U.S. Appl. No. 17/146,986, dated Mar. 11, 2021, 7 pages.

Strachan, Human Molecular Genetics 2 (Wiley-Liss, New York, 1999).

Vitale, 2019, An Optimized Workflow to Evaluate Estrogen Receptor Gene Mutations in Small Amounts of Cell-Fee DNA, The Journal of Molecular Diagnostics, 21(1):123-127.

Bowman, 2013, Multiplexed Illumina sequencing libraries from picogram quantities of DNA, BMC Genomics 14:466 (8 pages).

Eastburn, 2013, Ultrahigh-trhoughput mammalian single-cell reverse-transcriptase polymerase chain reaction in microfluidic drops, Anal Chem 85:8016-8021.

Figueiredo, 2007, Cost effective method for construction of high quality cDNA libraries, Biomol Eng 24:419-421.

Fu, 2015, Uniform and accurate single-cell sequencing based on emulsion whole-genome amplification, PNAS 112(38):11923-11928.

Int Search Report and Written Op dated Aug. 11, 2021, for Int Application No. PCT/US2021/022503, filed Mar. 16, 2021 (9 pages).

Int Search Report and Written Op dated Jun. 30, 2021, for Int Application No. PCT/US2021/023815, filed Mar. 24, 2021 (14 pages).

Kumaresan, 2008, High-throughput single copy DNA amplification and cell analysis in engineered nanoliter droplets, Anal Chem, 80:3522-3529.

Lage, 2003, Whole genome analysis of genetic alterations in small DNA samples using hyperbranched strand displacement amplification and array-CGH, Genome Res 13:294-307.

Lyons, 2017, Large-scale DNA barcode library generation for biomolecule identification in high-throughput screens, Sci Rep 7:13899 (7 pages).

Nishikawa, 2015, Monodisperse picoliter droplets for low-bias and contamination-free reactions in single-cell whole genome amplification, PLoSOne 10(9):e0138733 (15 pages).

Roche, 2011, emPCR amplificaiotn method manual, 454 Life Sciences Corp (12 pages).

Sidore, 2016, Enhanced sequencing coverage with digital droplet multiple displacement amplification, Nucl Acids Res 44(7):e66 (9 pages).

Stoeckius, 2017, Simultaneous epitope and transcriptome measurment in single cells, Nat Meth online pub (10 pages).

Tamminen, 2015, Single gene-based distinction of individual microbial genomes from a mixed population of microbial cells Front Microb 6:195 (10 pages).

(56) References Cited

OTHER PUBLICATIONS

Walls, 2020, Structure, Function, and Antigenicity of the SARS-CoV-2 Spike Glcoprotein, Cell, 181(2):281-292.
Zilionis, 2016, Single-cell barcoding and sequencing using droplet microfluidics, Natutre Prot 12(1):44-73.

* cited by examiner

MULTI-OMIC ANALYSIS IN MONODISPERSE DROPLETS

SEQUENCE LISTING

This application contains a sequence listing which has been submitted in ASCII format via EFS-Web and is hereby incorporated by reference. The ASCII-formatted sequence listing, created on May 28, 2021, is named FLBI-011-01US-Seq-listing-ST25.txt and is 790 bytes in size.

TECHNICAL FIELD

This disclosure relates to methods and systems for multi-omic profiling of single cells.

BACKGROUND

The complexity of biological systems necessitates the use of high-throughput assays to provide full characterization. For example, high-throughput methods are often implemented to reduce the number of individual experiments that need to be performed. Unfortunately, many methods for high-throughput analysis of single cells are constrained by costs associated with isolating single cells and preparing libraries.

Methods for isolating single cells generally require microfluidic devices that are complicated to use and expensive to operate. Moreover, since cells are processed individually, microfluidic devices are inherently limited in terms of the number of cells that can be assayed in a given experiment. Greater understanding of cell function and health often requires more than just genomic analysis. However, proteomic analysis and other studies require additional systems and experiments, adding further complication, time, and expense.

SUMMARY

This disclosure provides methods and systems for single-cell analysis, including single-cell multi-omic analysis, of target cells without microfluidic devices. Simultaneous analysis of both the transcriptome and proteome of single cells allows for thorough, efficient characterization of cell function. Systems and methods of the invention generate an emulsion with template particles to segregate individual target cells into monodisperse droplets without the need for expensive and complicated microfluidics. Nucleic acid molecules are released from the target cells inside the monodisperse droplets and are quantified to generate expression profiles for each of the target cells. Exposure of the cells to antibodies with conjugated nucleic acid tags allows for simultaneous proteomic analysis. Cell-bound antibodies are segregated into the monodisperse droplets along with the individual cells. In subsequent amplification and sequencing steps, the bound antibodies can be identified based on barcode sequences in the nucleic acid tags. Identification and quantification of the bound antibodies provides qualitative and quantitative information on surface protein expression in the cell. This approach provides a massively parallel analytical workflow that is inexpensive and scalable to ascertain multi-omic analysis of millions of single cells with a single library preparation.

Methods and systems of the invention use template particles to template the formation of monodisperse droplets and isolate target cells for profiling.

Methods include combining template particles with target cells in a first fluid, adding a second fluid to the first fluid, shearing the fluids to generate a plurality of monodisperse droplets simultaneously wherein each of the monodisperse droplets contain a single one of the template particles and a single one of the target cells. The target cells can be incubated with a mixture comprising one or more nucleic-acid-conjugated antibodies to allow antibody binding prior to droplet formation.

Nucleic-acid-conjugated antibodies comprise an antibody specific to a specific protein or class of proteins of interest (e.g., a surface protein of interest in single cell analysis) conjugated to a nucleic acid tag or label. The tag or label generally comprises DNA and can include a barcode that identifies the antibody (i.e., each different antibody used in an experiment is labelled with a unique barcode sequence associated only with that antibody). Presence of the barcode sequence in subsequent sequencing data is then indicative of the cellular expression of the protein targeted by the barcoded antibody. The tags or labels can additionally include a unique molecular identifier to provide quantitation of number of unique labeled antigens present on the target cell and a capture sequence. The capture sequence is a nucleic acid sequence that can be captured by barcode primers associated with the template particles in the droplets.

In multiplex proteomic/transcriptomic analyses, the capture sequence may advantageously comprise a poly A sequence that can be captured by poly T sequences already in use in capturing mRNA for gene expression analysis. Alternatively, the capture sequence may comprise a unique sequence that is specifically engineered to avoid competition with mRNA for capture at poly T sites. The tags or labels can also include a PCR handle for facilitating amplification of the label/primer hybrids. Many of the details of tagged antibody analysis of protein expression are similar to those used in CITE-seq as disclosed in Stoeckius, et al., 2017, Simultaneous epitope and transcriptome measurement in single cells, Nature Methods, 14:865-868, incorporated herein by reference.

After segregation in monodisperse droplets, the target cells can be lysed to release mRNA molecules which can then be captured and analyzed through, for example, reverse transcription, cDNA amplification, and sequencing along with the nucleic acid tags from target-cell-bound antibodies. In certain embodiments, mRNA quantification data can be used to create gene expression profiles for each of the target cells. The gene expression profiles can be used alone or together with the protein expression data to identify characteristics of the target cells that can be used to, for example, make a diagnosis, prognosis, or determine drug effectiveness.

Methods and systems of the invention provide a method for quantifying gene expression of target cells. The method includes releasing mRNA from target cells inside monodisperse droplets. The mRNA may be reverse transcribed into cDNA and simultaneously barcoded. The barcoded cDNA can be amplified to generate a plurality of barcoded amplicons. The amplicons can be sequenced by next generation sequencing methods, and because of the barcodes, each sequence read can be traced back to the target cell. The sequence reads are processed to generate an expression profile for the target cell.

After obtaining gene and protein expression profiles from target cells, the profiles may be analyzed by comparing the profiles with reference or control profiles to ascertain information about the target cells. In other instances, profiles of target cells can be compared to profiles derived from cells with certain phenotypes to determine whether the target cells share characteristics of the cells of the phenotype.

In certain aspects, the methods and systems of the invention provide a method for segregating cells into droplets. The cells may have been exposed to labelled antibody conjugates to bind target proteins prior to segregation. The droplets may be prepared as emulsions, e.g., as an aqueous phase fluid dispersed in an immiscible phase carrier fluid (e.g., a fluorocarbon oil, silicone oil, or a hydrocarbon oil) or vice versa. Generally, the droplets are formed by shearing two liquid phases. Shearing may comprise any one of vortexing, shaking, flicking, stirring, pipetting, or any other similar method for mixing solutions. Methods of the invention include combining cells with template particles in a first fluid, adding a second fluid, and shearing or agitating the first and second fluid. Preferably, the first fluid is an aqueous phase fluid, and, in some embodiments, may comprise reagents selected from, for example, buffers, salts, lytic enzymes (e.g. proteinase k) and/or other lytic reagents (e. g. Triton X-100, Tween-20, IGEPAL, or combinations thereof), nucleic acid synthesis reagents e.g. nucleic acid amplification reagents or reverse transcription mix, or combinations thereof.

Methods and systems of the invention use template particles to template the formation of monodisperse droplets and isolate target cells. Template particles according to aspects of the invention may comprise hydrogel, for example, selected from agarose, alginate, a polyethylene glycol (PEG), a polyacrylamide (PAA), acrylate, acrylamide/bisacrylamide copolymer matrix, azide-modified PEG, poly-lysine, polyethyleneimine, and combinations thereof. In certain instances, template particles may be shaped to provide an enhanced affinity for target cells. For example, the template particles may be generally spherical but the shape may contain features such as flat surfaces, craters, grooves, protrusions, and other irregularities in the spherical shape that promote an association with the target cell such that the shape of the template particle increases the probability of templating a droplet that contains the target cell.

In some aspects, methods and systems of the invention provide template particles that include one or more internal compartments. The internal compartments may contain a reagent or compound that is releasable upon an external stimulus. Reagents contained by the template particle may include, for example, cell lysis reagents or nucleic acid synthesis reagents (e.g., a polymerase). The external stimulus may be heat, osmotic pressure, or an enzyme. For example, in some instances, methods of the invention include releasing a reverse transcriptase directly inside of a droplet containing mRNA.

In certain aspects, this disclosure provides a kit for single cell profiling and nucleic acid sequencing. The kit includes template particles comprising a plurality of capture sequences specific to one or more genes of interest. The kit may include various labelled antibody conjugates or the components for preparing such conjugates. A researcher following instructions provided by the kit can use template particles and antibody conjugates to assay single cell expression of specific genes and proteins of interest, such as, oncogenes. Template particles and antibody conjugates may be custom designed for the user's specific needs, for example, designed to include capture probe sequences specific to the certain genes of interest, such as oncogenes or to target various proteins of interest. The template particles may be shipped inside sample preparation tubes, or sample collection tubes, such as blood collection tubes. The template particles are preferably in a dried or lyophilized format.

The kit may further include reagents, such as, cell lysis reagents, and nucleic acid synthesis reagents.

DETAILED DESCRIPTION

This disclosure provides systems and methods of using template particles to form monodisperse droplets for segregating single cells and preparing a library preparation thereof to profile expression of the single cells. The disclosed methods involve the use of template particles to template the formation of monodisperse droplets to generally capture a single target cell in an encapsulation, derive a plurality of distinct RNA from the single target cell, and prepare a library of nucleic acids that can be traced to the cell from which they were derived, and quantify distinct RNA to generate an expression profile of the single target cell. Methods of the invention can be used to prepare libraries for single cell analysis of, for example, at least 100 cells, at least 1000 cells, at least 1,000,000 cells, at least 2,000,000 cells, or more, from a single reaction tube.

By exposing cells to various nucleic-acid-labelled antibody conjugates prior to segregation in monodisperse droplets, subsequent amplification and sequencing can identify the expression profile of various target proteins by the target cell.

Figure 1:
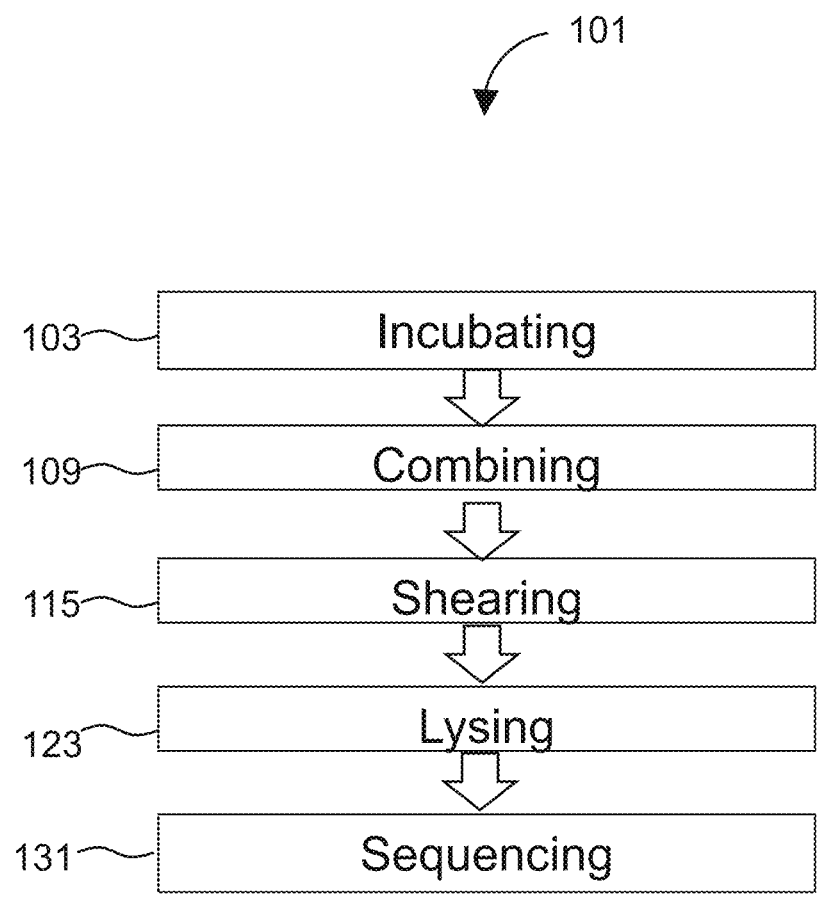
FIG. 1 diagrams a method for single cell profiling.

FIG. 1 diagrams a method 101 for single cell profiling. The method 101 includes incubating 103 target cells with nucleic-acid-labelled antibody conjugates. Incubation 103 can occur in the presence of a buffer promoting cell viability and antibody binding.

After incubating 103, the target cells are combined 109 template particles in a first fluid, and a second fluid immiscible with the first fluid is added to the mixture. The cells may be washed to remove unbound antibody conjugates before combination 109 with template particles. The first fluid is preferably an aqueous fluid. While any suitable order may be used, in some instances, a tube may be provided comprising the template particles. The tube can be any type of tube, such as a sample preparation tube sold under the trade name Eppendorf, or a blood collection tube, sold under the trade name Vacutainer. Template particles may be in dried format. Combining 109 may include using a pipette to pipette a sample comprising cells and, for example, the aqueous fluid into the tube containing template particles and then adding a second fluid that is immiscible, such as oil.

The method 101 then includes shearing 115 the fluids to generate monodisperse droplets, i.e., droplets. Preferably, shearing comprises agitating the tube containing the fluids using a vortexer or any method of controlled or uncontrolled agitation, such as shaking, pipetting, pumping, tapping, sonication and the like. After agitating (e.g., vortexing 115), a plurality (e.g., thousands, tens of thousands, hundreds of thousands, one million, two million, ten million, or more) of aqueous partitions is formed essentially simultaneously. Vortexing causes the fluids to partition into a plurality of monodisperse droplets. A substantial portion of droplets will contain a single template particle and a single target cell. Droplets containing more than one or none of a template particle or target cell can be removed, destroyed, or otherwise ignored.

The next step of the method 101 is to lyse 123 the target cells. Cell lysis 123 may be induced by a stimulus, such as, for example, lytic reagents, detergents, or enzymes. Reagents to induce cell lysis may be provided by the template particles via internal compartments. In some embodiments, lysing 123 involves heating the monodisperse droplets to a temperature sufficient to release lytic reagents contained inside the template particles into the monodisperse droplets. This accomplishes cell lysis 123 of the target cells, thereby releasing mRNA inside of the droplets that contained the target cells.

After lysing 123 target cells inside the droplets, mRNA is released and subsequently reverse transcribed and, along with the nucleic acid labels of surface-protein-bound antibody conjugates, amplified and sequenced 131. In order to sequence and quantify mRNA, reverse transcription is carried out to generate a library comprising cDNA with a barcode sequence that allows each library sequence to be traced back to the single cell from which the mRNA was derived. In preferred embodiments, template particles isolated with the mRNA include a plurality of barcoded capture sequences that hybridize with target mRNA. After hybridization, cDNA is synthesized by reverse transcription. Reagents for reverse transcription can be provided in a variety of ways in a variety of formats. In some instances, reagents and reverse transcriptase are provided by the template particles. Once a library is generated comprising barcoded cDNA, the cDNA can be amplified, by for example, PCR, to generate amplicons for sequencing 131.

The nucleic acid tags or labels of the antibody conjugates can include a PCR handle that functions as a primer site used for subsequent PCR amplification. Accordingly, the inclusion of PCR-handle-specific primers during amplification of the barcoded cDNA library will result in amplification of both mRNA-derived cDNA and antibody-conjugate-identifying labels for subsequent sequencing 131. In other embodiments, the nucleic acid tags or labels may comprise a poly A tag or other sequence complementary to the plurality of barcoded capture sequences present in or on the template particles. Inclusion of a poly A tag allows for the use of poly T barcoded capture sequences to hybridize both the nucleic acid tags or labels from bound antibody conjugates and mRNA from the lysed cell for gene expression profiling. Primer domains for subsequent PCR amplification can then be introduced to antibody tags as part of the capture sequence barcode that hybridize with target mRNA. Sequence reads are processed according to methods described herein to accomplish the quantification of mRNA and protein expression.

In some aspects, the target cells may include live cells obtained from, for example, a sample (tissue of bodily fluid) of a patient. The sample may include a fine needle aspirate, a biopsy, or a bodily fluid from the patient. Upon being isolated from the sample, the cells may be processed by, for example, generating a single cell suspension with an appropriate solution. Such solution will generally be a balanced salt solution, e.g. normal saline, PBS, Hank's balanced salt solution, etc., and in certain instances supplemented with fetal calf serum or other naturally occurring factors, in conjunction with an acceptable buffer at low concentration, generally from 5-25 mM. Convenient buffers include HEPES, phosphate buffers, lactate buffers, etc. The separated cells can be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscove's medium, etc., frequently supplemented with fetal calf serum.

Methods and systems of the invention use template particles to template the formation of monodisperse droplets and isolate single target cells. The disclosed template particles and methods for targeted library preparation thereof leverage the particle-templated emulsification technology previously described in, Hatori et. al., Anal. Chem., 2018 (90):9813-9820, which is incorporated by reference. Essentially, micron-scale beads (such as hydrogels) or "template particles" are used to define an isolated fluid volume surrounded by an immiscible partitioning fluid and stabilized by temperature insensitive surfactants.

The template particles of the present disclosure may be prepared using any method known in the art. Generally, the template particles are prepared by combining hydrogel material, e.g., agarose, alginate, a polyethylene glycol (PEG), a polyacrylamide (PAA), Acrylate, Acrylamide/bisacrylamide copolymer matrix, and combinations thereof. Following the formation of the template particles they are sized to the desired diameter. In some embodiments, sizing of the template particles is done by microfluidic co-flow into an immiscible oil phase.

In some embodiments of the template particles, a variation in diameter or largest dimension of the template particles such that at least 50% or more, e.g., 60% or more, 70% or more, 80% or more, 90% or more, 95% or more, or 99% or more of the template particles vary in diameter or largest dimension by less than a factor of 10, e.g., less than a factor of 5, less than a factor of 4, less than a factor of 3, less than a factor of 2, less than a factor of 1.5, less than a factor of 1.4, less than a factor of 1.3, less than a factor of 1.2, less than a factor of 1.1, less than a factor of 1.05, or less than a factor of 1.01.

Template particles may be porous or nonporous. In any suitable embodiment herein, template particles may include microcompartments (also referred to herein as "internal compartment"), which may contain additional components and/or reagents, e.g., additional components and/or reagents that may be releasable into monodisperse droplets as described herein. Template particles may include a polymer, e.g., a hydrogel. Template particles generally range from about 0.1 to about 1000 µm in diameter or larger dimension. In some embodiments, template particles have a diameter or largest dimension of about 1.0 µm to 1000 µm, inclusive, such as 1.0 µm to 750 µm, 1.0 µm to 500 µm, 1.0 µm to 250 µm, 1.0 µm to 200 µm, 1.0 µm to 150 µm 1.0 µm to 100 µm, 1.0 µm to 10 µm, or 1.0 µm to 5 µm, inclusive. In some embodiments, template particles have a diameter or largest dimension of about 10 µm to about 200 µm, e.g., about 10 µm to about 150 µm, about 10 µm to about 125 µm, or about 10 µm to about 100 µm.

In practicing the methods as described herein, the composition and nature of the template particles may vary. For instance, in certain aspects, the template particles may be microgel particles that are micron-scale spheres of gel matrix. In some embodiments, the microgels are composed of a hydrophilic polymer that is soluble in water, including alginate or agarose. In other embodiments, the microgels are composed of a lipophilic microgel.

In other aspects, the template particles may be a hydrogel. In certain embodiments, the hydrogel is selected from naturally derived materials, synthetically derived materials and combinations thereof. Examples of hydrogels include, but are not limited to, collagen, hyaluronan, chitosan, fibrin, gelatin, alginate, agarose, chondroitin sulfate, polyacrylamide, polyethylene glycol (PEG), polyvinyl alcohol (PVA), acrylamide/bisacrylamide copolymer matrix, polyacrylamide/poly(acrylic acid) (PAA), hydroxyethyl methacrylate (HEMA), poly N-isopropylacrylamide (NIPAM), and polyanhydrides, poly(propylene fumarate) (PPF).

In some embodiments, the presently disclosed template particles further comprise materials which provide the template particles with a positive surface charge, or an increased positive surface charge. Such materials may be without limitation poly-lysine or Polyethyleneimine, or combinations thereof. This may increase the chances of association between the template particle and, for example, a cell which generally have a mostly negatively charged membrane.

Other strategies may be used to increase the chances of templet particle-target cell association, which include creation of specific template particle geometry. For example, in some embodiments, the template particles may have a general spherical shape but the shape may contain features such as flat surfaces, craters, grooves, protrusions, and other irregularities in the spherical shape.

Any one of the above described strategies and methods, or combinations thereof may be used in the practice of the presently disclosed template particles and method for targeted library preparation thereof. Methods for generation of template particles, and template particles-based encapsulations, were described in International Patent Publication WO 2019/139650, which is incorporated herein by reference.

Creating template particle-based encapsulations for single cell expression profiling comprises combining target cells with a plurality of template particles in a first fluid to provide a mixture in a reaction tube. The mixture may be incubated to allow association of the plurality of the template particles with target cells. A portion of the plurality of template particles may become associated with the target cells. The mixture is then combined with a second fluid which is immiscible with the first fluid. The fluid and the mixture are then sheared so that a plurality of monodisperse droplets is generated within the reaction tube. The monodisperse droplets generated comprise (i) at least a portion of the mixture, (ii) a single template particle, and (iii) a single target particle. Of note, in practicing methods of the invention provided by this disclosure a substantial number of the monodisperse droplets generated will comprise a single template particle and a single target particle, however, in some instances, a portion of the monodisperse droplets may comprise none or more than one template particle or target cell.

In some embodiments, to increase the chances of generating an encapsulation, such as, a monodisperse droplet that contains one template particle and one target cell, the template particles and target cells are combined at a ratio wherein there are more template particles than target cells. For example, the ratio of template particles to target cells 213 combined in a mixture as described above may be in a range of 5:1 to 1,000:1, respectively. In other embodiments, the template particles and target cells are combined at a ratio of 10:1, respectively. In other embodiments, the template particles and target cells are combined at a ratio of 100:1, respectively. In other embodiments, the template particles and target cells are combined at a ratio of 1000:1, respectively.

To generate a monodisperse emulsion, the presently disclosed method includes a step of shearing the second mixture provided by combining a first mixture comprising target particles and target cells with a second fluid immiscible with the first mixture. Any suitable method or technique may be utilized to apply a sufficient shear force to the second mixture. For example, the second mixture may be sheared by flowing the second mixture through a pipette tip. Other methods include, but are not limited to, shaking the second mixture with a homogenizer (e.g., vortexer), or shaking the second mixture with a bead beater. In some embodiments, vortex may be performed for example for 30 seconds, or in the range of 30 seconds to 5 minutes. The application of a sufficient shear force breaks the second mixture into monodisperse droplets that encapsulate one of a plurality of template particles.

In some aspects, generating the template particles-based monodisperse droplets involves shearing two liquid phases. The mixture is the aqueous phase and, in some embodiments, comprises reagents selected from, for example, buffers, salts, lytic enzymes (e.g. proteinase k) and/or other lytic reagents (e. g. Triton X-100, Tween-20, IGEPAL, bm 135, or combinations thereof), nucleic acid synthesis reagents e.g. nucleic acid amplification reagents or reverse transcription mix, or combinations thereof. The fluid is the continuous phase and may be an immiscible oil such as fluorocarbon oil, a silicone oil, or a hydrocarbon oil, or a combination thereof. In some embodiments, the fluid may comprise reagents such as surfactants (e.g. octylphenol ethoxylate and/or octylphenoxypolyethoxyethanol), reducing agents (e.g. DTT, beta mercaptoethanol, or combinations thereof).

In practicing the methods as described herein, the composition and nature of the monodisperse droplets, e.g., single-emulsion and multiple-emulsion droplets, may vary. As mentioned above, in certain aspects, a surfactant may be used to stabilize the droplets. The monodisperse droplets described herein may be prepared as emulsions, e.g., as an aqueous phase fluid dispersed in an immiscible phase carrier fluid (e.g., a fluorocarbon oil, silicone oil, or a hydrocarbon oil) or vice versa. Accordingly, a droplet may involve a surfactant stabilized emulsion, e.g., a surfactant stabilized single emulsion or a surfactant stabilized double emulsion. Any convenient surfactant that allows for the desired reactions to be performed in the droplets may be used. In other aspects, monodisperse droplets are not stabilized by surfactants.

Figure 2:
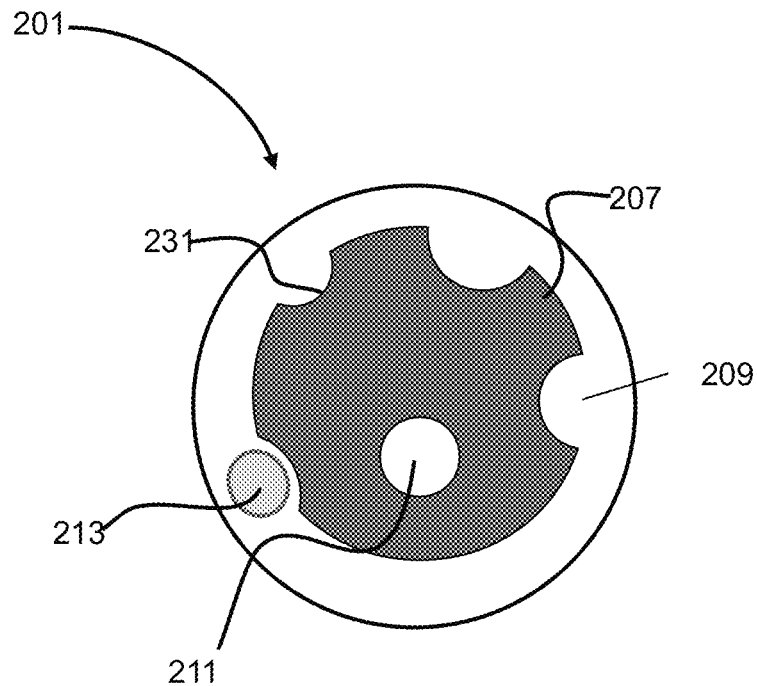
FIG. 2 illustrates a droplet according to one aspect of the invention.

FIG. 2 illustrates a droplet 201 according to one aspect of the invention. The depicted droplet 201 is a single one of a plurality of monodisperse droplets generated by shearing a mixture according to methods of the invention. The droplet 201 comprises a template particle 207 and a single target cell 213. The template particle 207 illustrated comprises crater-like depressions 231 to facilitate capture of single cells 213. The template particle 231 further comprises an internal compartment 211 to deliver one or more reagents into the droplet 201 upon stimulus. The target cell 213 may have optionally been exposed to nucleic-acid-labelled antibody conjugates prior to droplet formation. After washing away unbound antibody conjugates, the cell will carry along any bound antibody conjugates into the droplet 201 such that subsequent sequencing data showing the presence of one or more nucleic acid tags is indicative of the expression of that antibody conjugate's target protein by the target cell 213. Accordingly, a single amplification and sequencing reaction can provide quantitative and qualitative information regarding gene expression through mRNA analysis as well as protein expression data.

In some embodiments, the template particles contain multiple internal compartments. The internal compartments of the template particles may be used to encapsulate reagents that can be triggered to release a desired compound, e.g., a substrate for an enzymatic reaction, or induce a certain result, e.g. lysis of an associated target cell. Reagents encapsulated in the template particles' compartment may be without limitation reagents selected from buffers, salts, lytic enzymes (e.g. proteinase k), other lytic reagents (e. g. Triton X-100, Tween-20, IGEPAL, bm 135), nucleic acid synthesis reagents, or combinations thereof.

Lysis of single target cells occurs within the monodisperse droplets and may be induced by a stimulus such as heat, osmotic pressure, lytic reagents (e.g., DTT, beta-mercaptoethanol), detergents (e.g., SDS, Triton X-100, Tween-20), enzymes (e.g., proteinase K), or combinations thereof. In some embodiments, one or more of the said reagents (e.g., lytic reagents, detergents, enzymes) is compartmentalized within the template particle. In other embodiments, one or more of the said reagents is present in the mixture. In some other embodiments, one or more of the said reagents is added to the solution comprising the monodisperse droplets, as desired.

Figure 3:
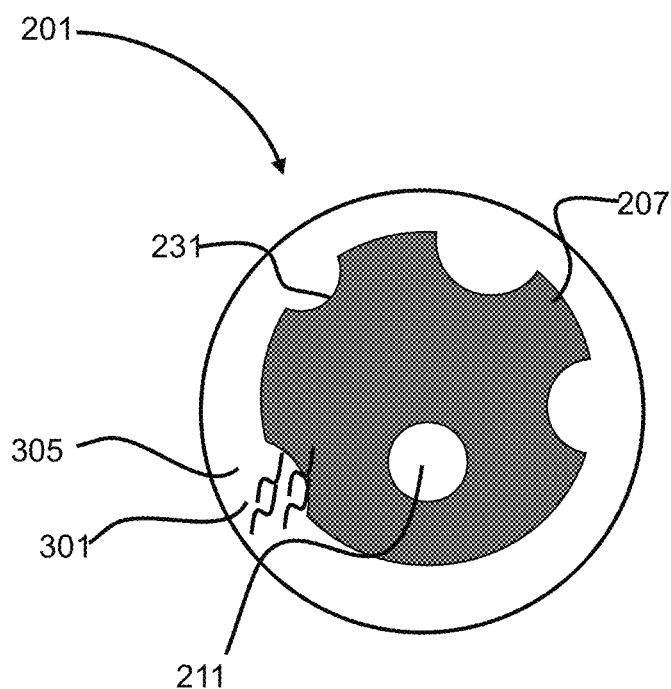
FIG. 3 illustrates a droplet following lysis of a target cell.

FIG. 3 illustrates a droplet 201 following lysis of a target cell. The depicted droplet 201 comprises a template particle 207 and released mRNA 301 and nucleic acid tags 305 from antibody conjugates that had bound target proteins on the lysed target cell. Methods of the invention quantify amplified products of the released mRNAs 301 and nucleic acid tags 305, preferably by sequencing.

In preferred embodiments, template particles comprise a plurality of capture probes. Generally, the capture probe of the present disclosure is an oligonucleotide. In some embodiments, the capture probes are attached to the template particle's material, e.g. hydrogel material, via covalent acrylic linkages. In some embodiments, the capture probes are acrydite-modified on their 5' end (linker region). Generally, acrydite-modified oligonucleotides can be incorporated, stoichiometrically, into hydrogels such as polyacrylamide, using standard free radical polymerization chemistry, where the double bond in the acrydite group reacts with other activated double bond containing compounds such as acrylamide. Specifically, copolymerization of the acrydite-modified capture probes with acrylamide including a crosslinker, e.g. N,N'-methylenebis, will result in a crosslinked gel material comprising covalently attached capture probes. In some other embodiments, the capture probes comprise Acrydite terminated hydrocarbon linker and combining the said capture probes with a template particle will cause their attachment to the template particle.

Figure 4:
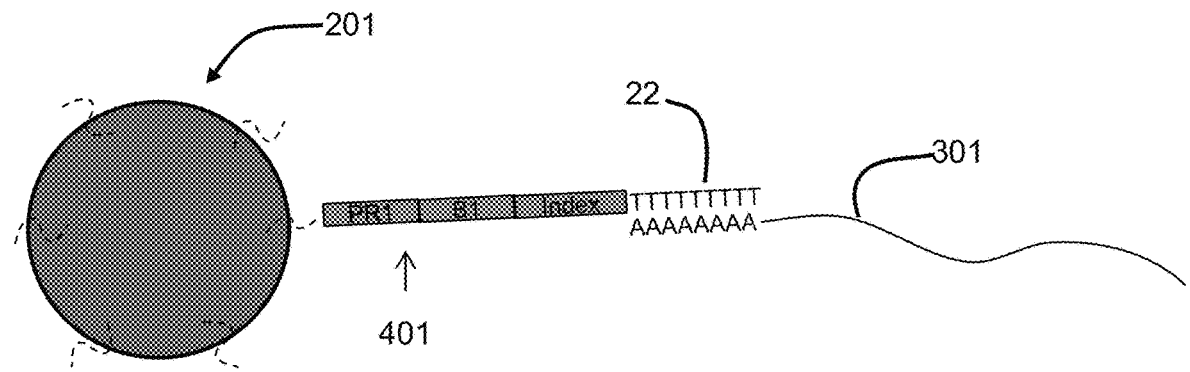
FIG. 4 illustrates the capture of mRNA.
Figure 5:
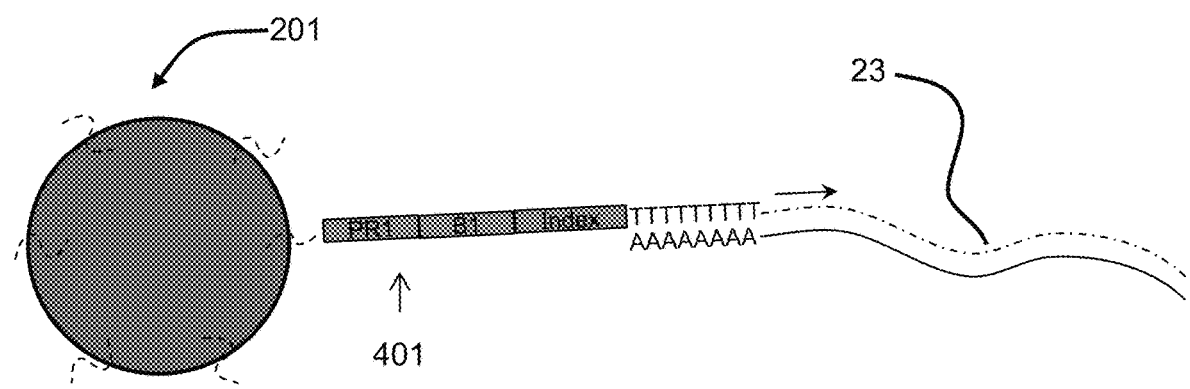
FIG. 5 illustrates synthesis of cDNA to form a first strand.
Figure 6:
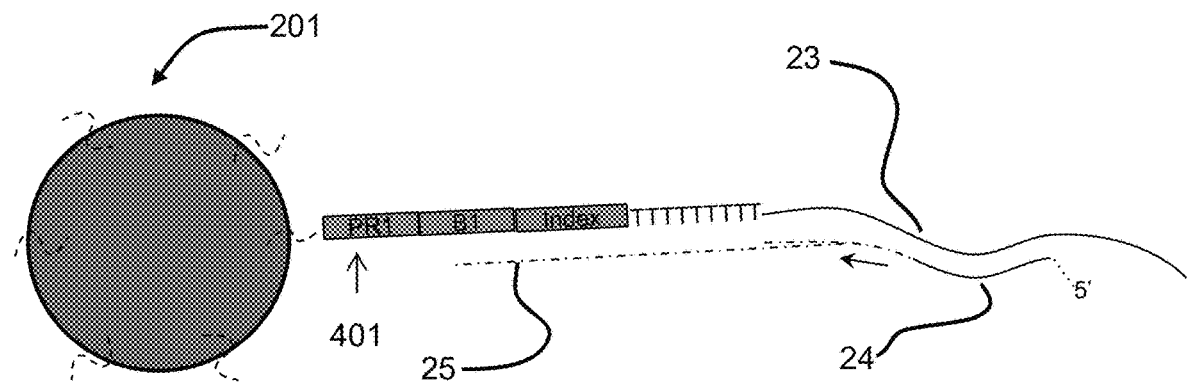
FIG. 6 illustrates amplification of a first strand to generate an amplicon.

FIGS. 4-6 show an exemplary method for nonspecific amplification of mRNA according to certain aspects of the disclosure. In particular, the method relies on the presence of a poly A tail at the 3' end of a mRNA for the non-specific capture of mRNAs. A poly A sequence may be included in the nucleic acid labels of the antibody conjugates so that the same capture probes can capture both target mRNA and target antibody labels.

FIG. 4 illustrates the capture of mRNA 301 but can be similarly applied to the capture of target antibody conjugate labels which can occur simultaneously for multi-omic analysis. Shown, is a template particle 201 comprising a plurality of capture probes 401 illustrated schematically by curved broken lines. One of the capture probes 401 is featured in a larger scale and in detail. The capture probe 401 preferably comprises, from 5' end to 3' end, a linker region to allow covalent bond with the template particle 201, a PR1 nucleotide sequence region comprising a universal primer nucleotide sequence, at least one barcode region B1, which may include an index nucleotide sequence index, and/or a UMI, the capture probe 201 further including a capture nucleotide sequence 22 comprising a poly T nucleotide sequence. A released nucleic acid, i.e., mRNA molecule 301 comprising a poly A sequence attaches to the capture probe's poly T sequence 22 via complementary base pairing. Following the hybridization of the mRNA molecule 301 and the capture probe 401, a reverse transcriptase is used to perform a reverse transcription reaction to synthesize cDNA and thereby create a first strand comprising the cDNA and the capture probe sequence. Nucleic acid tags from the antibody conjugates will be similarly captured due to the inclusion of a poly A sequence and, in the case of an RNA nucleic acid tag, can undergo reverse transcription along with the captured mRNA from the target cell. In the case of a DNA nucleic acid tag, the tags will not undergo reverse transcription and will simply remain bound to the template particle 201 via a capture probe 401 and await subsequent amplification along with cDNA synthesized from the captured mRNA 301.

FIG. 5 illustrates synthesis of cDNA to form a first strand 23. A reverse transcriptase (not shown) synthesizes cDNA from mRNA that is hybridized to a poly T sequence of a capture probe 401. After synthesis, a first strand 23 is formed, wherein the first strand 23 comprises the cDNA and the capture probe 401 sequence. Following synthesis, the mRNA molecule 301-first strand 23 hybrid may be denatured (not shown) using any method traditional in the art, such as an exposure to a denaturing temperature.

FIG. 6 illustrates amplification of a first strand to generate an amplicon. In particular, following the formation of a first strand 23, a second strand primer 24 comprising a random sequence, such as, a random hexamer, anneals with the first strand 23 to form a DNA-primer hybrid. A DNA polymerase is used to synthesize a complementary second strand 25, i.e., an amplicon. In the embodiment illustrated, the second strand primer 24 comprises a "tail" region which does not hybridize with the first strand 23. In some embodiments, the tail region comprises a second universal primer sequence. The second strand 25 may be further amplified by PCR to generate a plurality of amplicons, and quantified by DNA sequencing. Similar universal primer sequence can be included in the nucleic acid tags from the antibody conjugates such that those tags will be simultaneously amplified using the same primers as the mRNA-derived cDNA.

Amplification or nucleic acid synthesis, as used herein, generally refers to methods for creating copies of nucleic acids by using thermal cycling to expose reactants to repeated cycles of heating and cooling, and to permit different temperature-dependent reactions (e.g. by polymerase chain reaction (PCR)). Any suitable PCR method known in the art may be used in connection with the presently described methods. Non limiting examples of PCR reactions include real-time PCR, nested PCR, multiplex PCR, quantitative PCR, TS-PCR, or touchdown PCR.

The terms "nucleic acid amplification reagents" or "reverse transcription mix" encompass without limitation dNTPs (mix of the nucleotides dATP, dCTP, dGTP and dTTP), buffer/s, detergent/s, or solvent/s, as required, and suitable enzyme such as polymerase or reverse transcriptase. The polymerase used in the presently disclosed targeted library preparation method may be a DNA polymerase, and may be selected from, but is not limited to, Taq DNA polymerase, Phusion polymerase, or Q5 polymerase. The reverse transcriptase used in the presently disclosed targeted library preparation method may be for example, Moloney murine leukemia virus (MMLV) reverse transcriptase, or maxima reverse transcriptase. In some embodiments, the general parameters of the reverse transcription reaction comprise an incubation of about 15 minutes at 25 degrees and a subsequent incubation of about 90 minutes at 52 degrees. Nucleic acid amplification reagents are commercially available, and may be purchased from, for example, New England Biolabs, Ipswich, MA, USA, or Clonetech.

Figure 7:
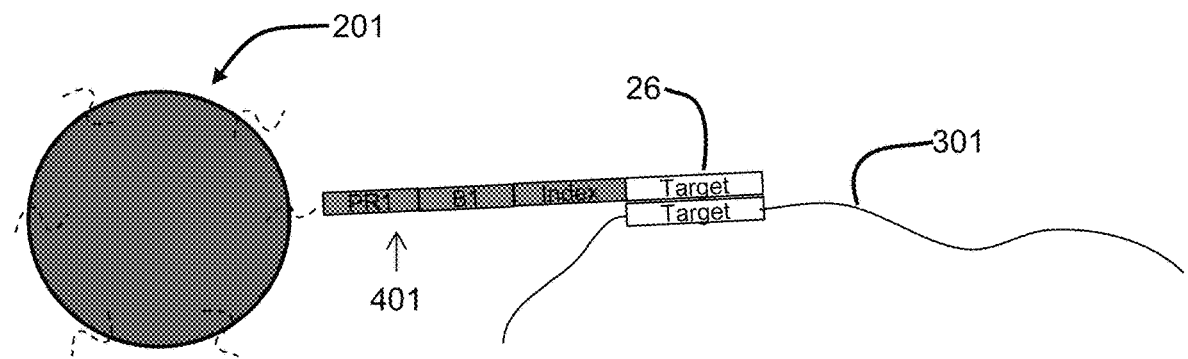
FIG. 7 illustrates a method for sequence-specific capture of mRNA.
Figure 8:
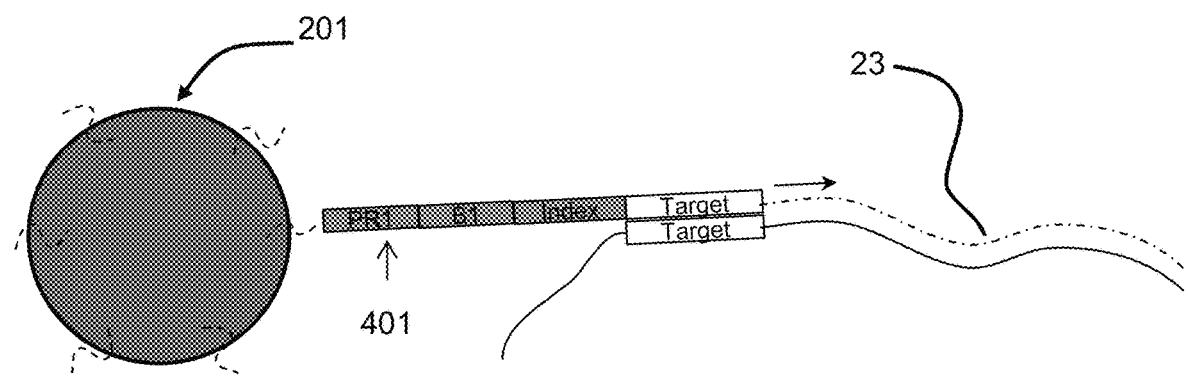
FIG. 8 illustrates synthesis of cDNA to form a first strand.
Figure 9:
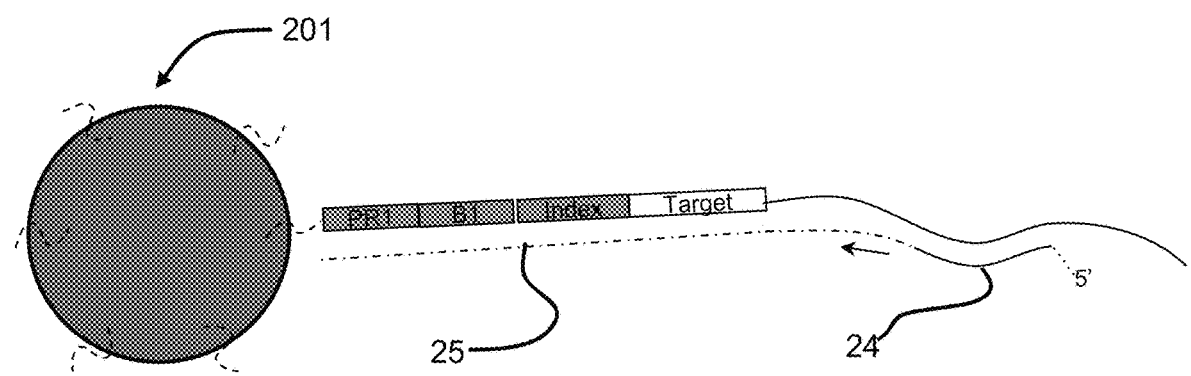
FIG. 9 illustrates amplification of a first strand to generate an amplicon.

FIGS. 7-9 illustrate a method for sequence-specific amplification of mRNA according to certain aspects of the disclosure but can be similarly applied to the capture of target antibody conjugate labels which can occur simultaneously for multi-omic analysis.

FIG. 7 illustrates a method for sequence-specific capture of mRNA 301. The template particle 201 comprises a plurality of capture probes 401 illustrated schematically by curved broken lines. A featured capture probe 401 comprises, from 5' end to 3' end, a linker region to allow covalent bond with the template particle 201, a PR1" region comprising a universal primer nucleotide sequence, at least one barcode region B1, which may include an index sequence, and/or a UMI, the capture probe 401 further comprising and a capture sequence comprising a gene-specific sequence 26. Capture probes 401 can be included wherein the gene-specific sequence 26 is substituted with various complementary sequences to barcodes or tags included in the nucleic acid tags of the antibody conjugates. By using separate capture sequences, competition for binding between mRNA and antibody tags can be avoided along with resulting bias in the data. A molecule of mRNA 301, released inside a monodisperse droplet, comprising a sequence complementary to the gene-specific sequence 26 attaches to the capture probe's gene-specific sequence 26 via complementary base pairing. The gene-specific or transcript-specific sequence may comprise any sequence of interest, for example, a sequence corresponding to an oncogene.

For example, in some instances template particles 201 according to aspects of the invention may comprise capture probes with certain sequences specific to genes of interest, such as, oncogenes. Some non-limiting examples of genes of interest that may be assayed for include, but are not limited to, BAX, BCL2L1, CASP8, CDK4, ELK1, ETS1, HGF, JAK2, JUNB, JUND, KIT, KITLG, MCL1, MET, MOS, MYB, NFKBIA, EGFR, Myc, EpCAM, NRAS, PIK3CA, PML, PRKCA, RAF1, RARA, REL, ROS1, RUNX1, SRC, STAT3, CD45, cytokeratins, CEA, CD133, HER2, CD44, CD49f, CD146, MUC1/2, ABL1, AKT1, APC, ATM, BRAF, CDH1, CDKN2A, CTNNB1, EGFR, ERBB2, ERBB4, EZH2, FBXW7, FGFR2, FGFR3, FLT3, GNAS, GNAQ, GNA11, HNF1A, HRAS, IDH1, IDH2, JAK2, JAK3, KDR, KIT, KRAS, MET, MLH1, NOTCH1, NPM1, NRAS, PDGFRA, PIK3CA, PTEN, PTPN11, RB1, RET, SMAD4, STK11, TP53, VHL, and ZHX2.

FIG. 8 illustrates the synthesis of cDNA to form a first strand 23. A reverse transcriptase (not shown) synthesizes cDNA from mRNA that is hybridized to gene-specific sequence of a capture probe 12. Following the hybridization of the target mRNA molecule 301 and the capture probe 12, a reverse transcription reaction is performed to synthesize cDNA and create a first strand 23. The first strand 23 comprises synthesized cDNA and the capture probe 401 sequence. The target mRNA molecule-first strand hybrid is then denatured using methods traditional in the art (not shown), and second strand primer 24 comprising a random hexamer sequence anneals with complementary sequence of the first strand 23 to form a DNA-primer hybrid.

FIG. 9 illustrates amplification of a first strand 23 to generate an amplicon 25. In particular, following the formation of a first strand 23, a second strand primer 24 comprising a random sequence, such as, a random hexamer, anneals with the first strand 23 to form a DNA-primer hybrid. A DNA polymerase is used to synthesize a complementary second strand 25, i.e., an amplicon 25. In the embodiment illustrated, the second strand primer 24 comprises a "tail" region which does not hybridize with the first strand 23. In some embodiments, the tail region comprises a second universal primer sequence.

According to aspects of the present disclosure, the term "universal primer sequence" generally refers to a primer binding site, e.g., a primer sequence that would be expected to hybridize (base-pair) to, and prime, one or more loci of complementary sequence, if present, on any nucleic acid fragment. In some embodiments, the universal primer sequences used with respect to the present methods are P5 and P7.

The term barcode region may comprise any number of barcodes, index or index sequence, UMIs, which are unique, i.e., distinguishable from other barcode, or index, UMI sequences. The sequences may be of any suitable length which is sufficient to distinguish the barcode, or index, sequence from other barcode sequences. A barcode, or index, sequence may have a length of 4, 5, 6, 7, 8, 9, 10, 11, 12, 13, 14, 15, 16, 17, 18, 19, 20, 21, 22, 23, 24, 25 nucleotides, or more. In some embodiments, the barcodes, or indices, are predefined and selected at random.

In some methods of the invention, a barcode sequence may comprise unique molecular identifiers (UMIs). UMIs are a type of barcode that may be provided to a sample to make each nucleic acid molecule, together with its barcode, unique, or nearly unique. This may be accomplished by adding one or more UMIs to one or more capture probes of the present invention. By selecting an appropriate number of UMIs, every nucleic acid molecule in the sample, together with its UMI, will be unique or nearly unique.

UMIs are advantageous in that they can be used to correct for errors created during amplification, such as amplification bias or incorrect base pairing during amplification. For example, when using UMIs, because every nucleic acid molecule in a sample together with its UMI or UMIs is unique or nearly unique, after amplification and sequencing, molecules with identical sequences may be considered to refer to the same starting nucleic acid molecule, thereby reducing amplification bias. Methods for error correction using UMIs are described in Karlsson et al., 2016, "Counting Molecules in cell-free DNA and single cells RNA", Karolinska Institutet, Stockholm Sweden, incorporated herein by reference.

Such UMIs, present in the nucleic acid tags of antibody conjugates according to the invention, can allow for relative quantification of various expression of proteins by the target cell by permitting the grouping of antibody tag amplicons by molecule of origin.

Figure 10:
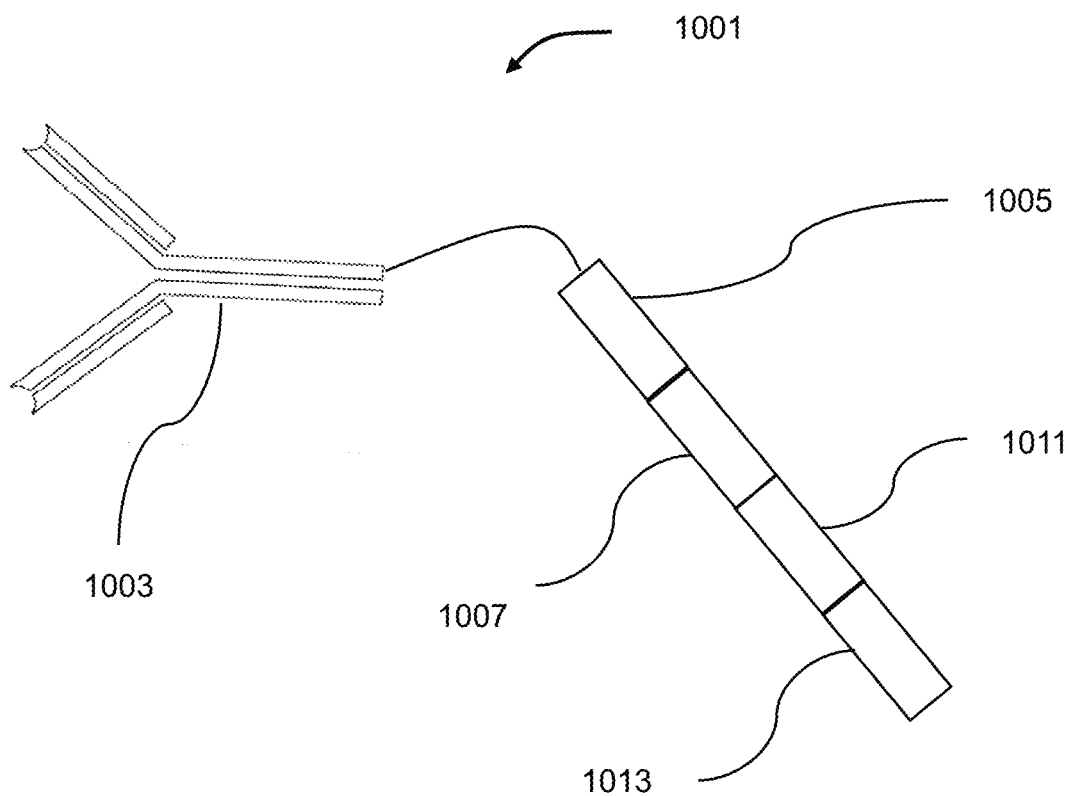
FIG. 10 shows an exemplary nucleic-acid-labelled antibody conjugate.

For proteomic analysis, cell samples can be incubated with a mixture comprising one or more labeled antibody conjugates. An exemplary antibody conjugate is shown in FIG. 10. Additional antibody conjugates and processes for their use in multi-omic analysis along with mRNA gene expression profiling can be found in descriptions of CITE-seq including Stoeckius, et al., 2017, Simultaneous epitope and transcriptome measurement in single cells, Nature Methods, 14:865-868.

As shown in FIG. 10, labelled antibody conjugates 1001 may include an antibody 1003 which can be selected based on the target protein to be analyzed. For example, where expression of a certain surface protein, or lack thereof, is indicative of a certain disease, antibodies 1003 that specifically bind that surface protein may be used. Linked to the antibody 1003 is a nucleic acid tag or label that may comprise various sequence portions. For example, as shown in FIG. 10, the nucleic acid tag or label may include a PCR handle 1005 or universal primer site used for subsequent PCR amplification as discussed above. The nucleic acid tag or label may include a barcode 1007 that is specific to the antibody 1003 to which it is linked and can be used to subsequently identify the antibody 1003 in by sequence analysis. Additional components may include a UMI 1011 which can be used where multiple copies of a single type of antibody conjugate 1001 are used in order to collapse sequencing reads and remove amplification or sequencing or errors in quantifying protein expression. The tag may also include a capture portion 1013 that is complementary to the capture sequence on template particles to allow capture of the tags 1001 for subsequent amplification and the potential addition of further adapter sequences in a similar fashion as described with respect to the mRNA methods above. In preferred embodiments, the capture portion comprises a poly A sequence to allow poly T capture probes to be used to hybridize both mRNA and antibody conjugate tags for multi-omic analysis.

Incubation of target cells with the labelled antibody conjugates can occur in a buffer that promotes cell viability and reliable antibody conjugation. Cells may be washed post-incubation to remove any unbound antibody conjugates. The antibody labeled cells can then be put in suspension with template particles and separated into monodisperse droplets as described above for cell capture, lysis, and mRNA hybridization as described above.

At this stage, antibody tags will be captured by their appropriate capture probes alongside mRNA from the lysed target cell. Emulsions can then be broken, the templates washed, and cDNA generated by reverse transcription. The cDNA can then be amplified which should generate the profile of captured cDNA as described but should also generate a significant population of short sequences that contain antibody tags. Additive primers may be added to the cDNA PCR to increase yield of antibody DNA labels. Antibody tags may be identified by qPCR as a control check. The PCR products can then be purified and sequenced using known sequencing techniques (e.g., Illumina sequencing).

Alternative Multi-Omics Approaches

In certain embodiments, specific antibodies may be conjugated directly to the template particles in order to allow for selective cell or particle capture based on surface antigen identity. In such cases, a library of specific labeled template particles can be incubated with a population of cells, and the type of captured cell may then be determined by barcode elements that identify the antigen capture probe on the template particle. Such embodiments may be particularly useful for applying template particle capture techniques to non-mammalian cell systems, including viral or bacterial detection.

Other capture probes may also be included on template particles depending on the desired application, including small molecule drugs to select for particular receptors, RNA derived aptamers, or DNA sequences for specific hybridization of targeted DNA sequences.

In certain aspects, methods of the invention include combining template particles with target cells in a first fluid, adding a second fluid to the first fluid, shearing the fluids to generate a plurality of monodisperse droplets simultaneously that contain a single one of the template particles and a single one of the target cells, in which the template particles preferably include one or more oligos useful in template switching oligo (TSO) embodiments. The method preferably also includes lysing each of the single target cells contained within the monodisperse droplets to release a plurality of distinct mRNA molecules; and quantifying the plurality of distinct mRNA molecules by, for example, using template switching PCR (TS-PCR), as discussed in U.S. Pat. No. 5,962,272, which is incorporated herein by reference. TS-PCR is a method of reverse transcription and polymerase chain reaction (PCR) amplification that relies on a natural PCR primer sequence at the polyadenylation site, also known as the poly(A) tail, and adds a second primer through the activity of murine leukemia virus reverse transcriptase. This method permits reading full cDNA sequences and can deliver high yield from single sources, even single cells that contain 10 to 30 picograms of mRNA.

TS-PCR generally relies on the intrinsic properties of Moloney murine leukemia virus (MMLV) reverse transcriptase and the use of a unique TSO. During first-strand synthesis, upon reaching the 5' end of the mRNA template, the terminal transferase activity of the MMLV reverse transcriptase adds a few additional nucleotides (mostly deoxycytidine) to the 3' end of the newly synthesized cDNA strand. These bases may function as a TSO-anchoring site. After base pairing between the TSO and the appended deoxycytidine stretch, the reverse transcriptase "switches" template strands, from cellular RNA to the TSO, and continues replication to the 5' end of the TSO. By doing so, the resulting cDNA contains the complete 5' end of the transcript, and universal sequences of choice are added to the reverse transcription product. This approach makes it possible to efficiently amplify the entire full-length transcript pool in a completely sequence-independent manner.

Figure 11:
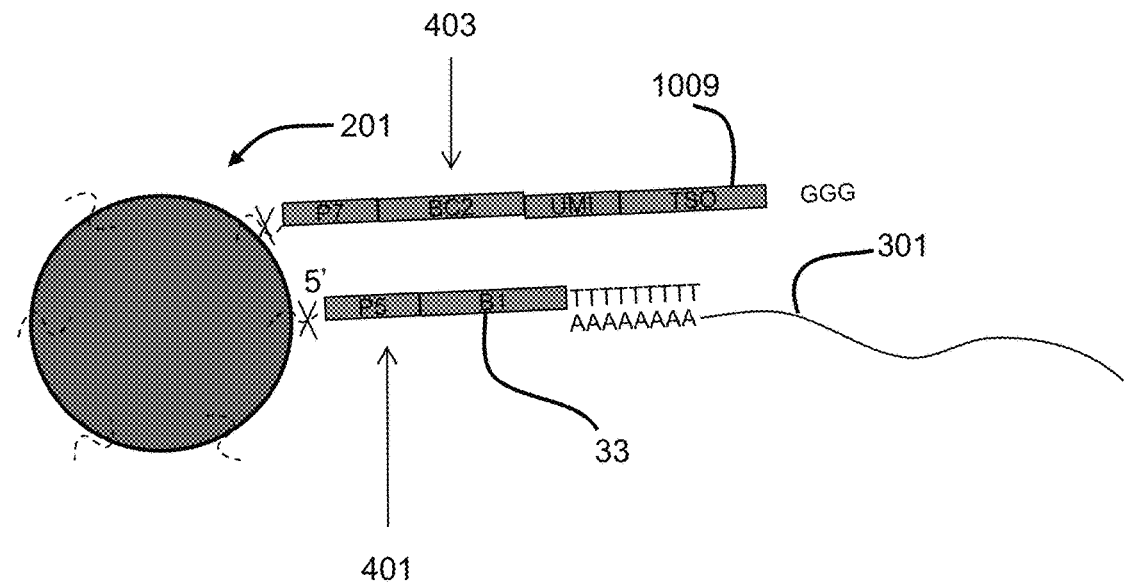
FIG. 11 illustrates the capture of mRNA according to TSO embodiments.

FIG. 11 illustrates the capture of mRNA 301 according to TSO embodiments. The TSO 1009 is an oligo that hybridizes to untemplated C nucleotides added by the reverse transcriptase during reverse transcription. The TSO may add, for example, a common 5' sequence to full length cDNA that is used for downstream cDNA amplification. Shown, is a template particle 201 that comprises a first capture probe 401, and a second capture probe 403. The first capture probe 401 preferably comprises, from 5' end to 3' end, a linker region to allow a covalent bond with the template particle 201, a P5 nucleotide sequence region comprising a universal primer nucleotide sequence, at least one barcode 33, and a capture nucleotide sequence 22 comprising a poly T nucleotide sequence. The second capture probe 403 preferably includes a TSO 1009, a UMI, a second barcode, a P7 nucleotide sequence region comprising a universal primer nucleotide sequence. A released nucleic acid, i.e., mRNA molecule 301 comprising a poly A sequence attaches to the first capture probe's 401 poly T sequence 22 via complementary base pairing. Following the hybridization of the mRNA molecule 301 and the capture probe 401, TS-PCR is performed using a reverse transcriptase, i.e., murine leukemia virus reverse transcriptase, to synthesize cDNA and thereby create a first strand. During TS-PCR amplification, upon reaching the 5' end of the mRNA template, the terminal transferase activity of the reverse transcriptase adds a few additional nucleotides (mostly deoxycytidine), to the 3' end of the nascent first strand.

Figure 12:
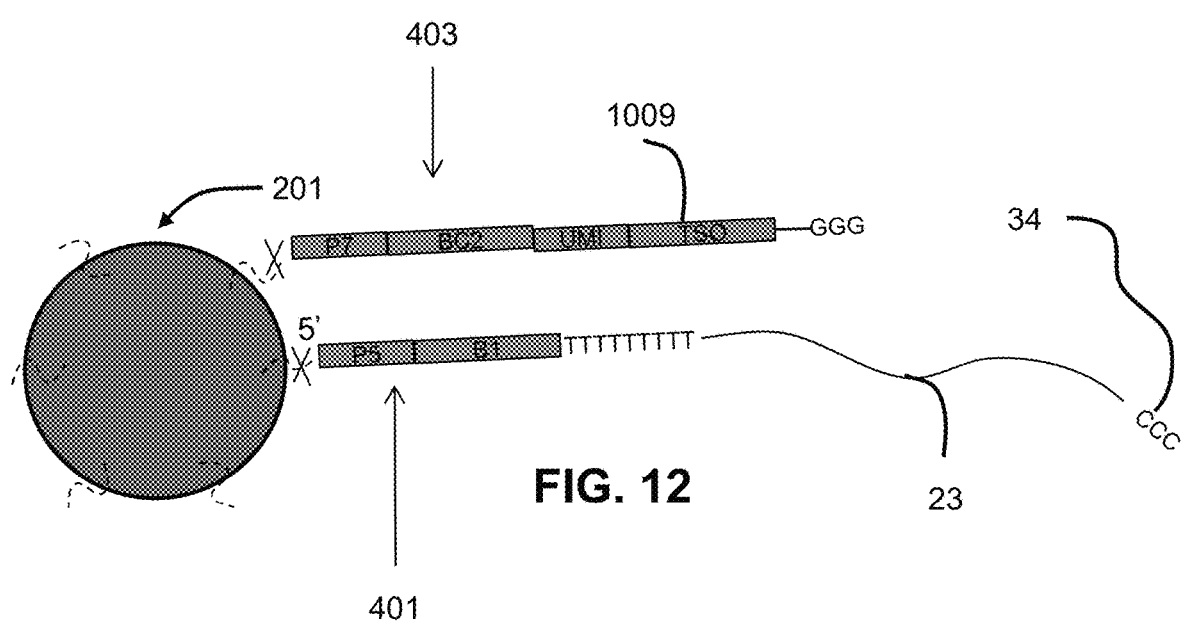
FIG. 12 shows a first strand following TSO-PCR amplification.

FIG. 12 shows a first strand 23 following TS-PCR amplification. The first strand 23 includes additional nucleotides that may function as a TSO-anchoring site 34. The TSO-anchoring site 34 may hybridize with the TSO 1009, after base pairing between the TSO and the TSO-anchoring site 34, the reverse transcriptase "switches" template strands, from cellular RNA to the TSO, and continues replication to the 5' end of the TSO. By doing so, the resulting cDNA contains the complete 5' end of the transcript, and sequences from the second capture probe 403. after synthesis of the first strand 23, the first strand 23 including capture probes 401, 403, may be released either by cleaving covalent bonds attaching the capture probes 401, 403 to a surface of the template particle 201, or by dissolving the template particle 201, for example, by heat.

A person with ordinary skills in the art will appreciate that any one of the template particle embodiments, capture probes, primer probes, second strand primers, universal amplification primers, barcodes, UMIs, TSOs, and methods thereof described in any one of the embodiments of the presently disclosed targeted library preparation method may be used in a different combination, or embodiment, of the present method. For example, any one of the presently described second strand primers, or primer probe, may be used to prime any one of the presently disclosed first strand to allow for a DNA synthesis reaction to generate an amplicon.

In preferred embodiments, quantifying released mRNA comprises sequencing, which may be performed by methods known in the art. For example, see, generally, Quail, et al., 2012, A tale of three next generation sequencing platforms: comparison of Ion Torrent, Pacific Biosciences and Illumina MiSeq sequencers, BMC Genomics 13:341. Nucleic acid sequencing techniques include classic dideoxy sequencing reactions (Sanger method) using labeled terminators or primers and gel separation in slab or capillary, or preferably, next generation sequencing methods. For example, sequencing may be performed according to technologies described in U.S. Pub. 2011/0009278, U.S. Pub. 2007/0114362, U.S. Pub. 2006/0024681, U.S. Pub. 2006/0292611, U.S. Pat. Nos. 7,960,120, 7,835,871, 7,232,656, 7,598,035, 6,306,597, 6,210,891, 6,828,100, 6,833,246, and 6,911,345, each incorporated by reference.

The conventional pipeline for processing sequencing data includes generating FASTQ-format files that contain reads sequenced from a next generation sequencing platform, aligning these reads to an annotated reference genome, and quantifying expression of genes. These steps are routinely performed using known computer algorithms, which a person skilled in the art will recognize can be used for executing steps of the present invention. For example, see Kukurba, Cold Spring Harb Protoc, 2015 (11):951-969, incorporated by reference.

After obtaining expression profiles from single cells, the expression profiles can be analyzed by, for example, comparing the profiles with reference or control profiles to ascertain information about the single target cells. For example, see generally, Efroni, Genome Biology, 2015; and Stahlberg, Nucleic Acids Research, 2011, 39(4)e24, each of which incorporated by reference.

In one aspect, methods and systems of the invention provide a method for identifying a rare cell from a heterogeneous cell population. The method includes isolating a plurality of single target cells from the heterogeneous cell population by combining the heterogeneous cells with a plurality of template particles in a first fluid, adding a second fluid that is immiscible with the first fluid, and shearing the fluids to generate an emulsion comprising monodisperse droplets that each contain a single target cell and a single template particle. Antibody conjugates may also be included before emulsion generation such that isolation of target cells in the heterogeneous cell population will also isolate target-protein-bound antibody conjugates for incorporation in the monodisperse droplets. Methods may further include releasing a plurality of mRNA molecules from each of the single target cells contained within the monodisperse droplets and quantifying the plurality of mRNA molecules along with identifying and quantifying the expressed target proteins based on the presence and amount of antibody conjugate labels sequenced. Quantifying may include generating a plurality of amplicons of the mRNA molecules wherein each of the amplicons comprise a barcode or index sequence that is unique to the cell from which the mRNA molecule was derived. In some instances, methods may include sequencing the plurality of barcoded amplicons by, for example, next-generation sequencing methods to generate sequence reads for each of the amplicons. Methods may further include processing the sequence reads associated with single cells of the heterogeneous cell population to generate expression profiles for each of the single cells and using the data by, for example, performing a gene clustering analysis to identify one or more cell types or cell states.

In another aspect, methods and systems of the disclosure provide a method for analyzing a heterogeneous tumor biopsy taken from a subject. The method includes obtaining a biopsy from a patient and isolating a population of cells from the biopsy. The method further includes segregating the population of cells taken from the biopsy into droplets by combining the population of cells with a plurality of template particles in a first fluid (with the optional inclusion of antibody conjugates), adding a second fluid that is immiscible with the first fluid, and shearing the fluids to generate an emulsion comprising monodisperse droplets that each contain a single one of the population of cells and a single template particle. Methods further include releasing a plurality of mRNA molecules from each one of the segregated single cells contained within the monodisperse droplets and performing transcriptome analysis on one or more genes of the single cells and using the transcriptome data and/or the proteomic data from bound antibody conjugates to identify one or more characteristics of the tumor. A characteristic identified can be the presence, or absence, of one or more gene transcripts or proteins associated with a cancer. A method disclosed herein can further comprise the step of using the characteristic to diagnose a subject with cancer or a cancer stage or to devise a treatment plan.

In some aspects, methods and systems of the invention provide a method for determining the potential effectiveness of a therapeutic agent. The method comprises segregating a first population of antibody conjugate bound, diseased cells into monodisperse droplets with template particles and determining the expression level of at least one nucleic acid and/or at least one protein from at least one of the diseased cells, thereby producing a disease-state expression signature. The method further includes exposing a second population of disease state cells to an agent and determining the expression level of at the least one nucleic acid and/or protein from at least one of the individual cells from the second population and comparing the expression level from the individual cell from the second population to the disease-state expression signature to thereby determine the effectiveness of the agent against the disease. In some embodiments, the therapeutic agent may be delivered to a second population of cells inside monodisperse droplets. For example, the agent may be associated with the template particle by tethering the agent to an external surface of the template particle, or packaging the agent inside a compartment of the template particle such that the agent can be delivered to the cells contained inside the monodisperse droplets.

In any one of the embodiments of the presently disclosed targeted library preparation method, the template particle further comprises a capture moiety. In some embodiments, the capture moiety acts to capture specific target particles, for example, specific types of cells. In some embodiments, the capture moiety comprises an Acrylate-terminated hydrocarbon linker with biotin termination. In some embodiments, the capture moiety is attached to a target-specific capture element. In some embodiments, the target-specific capture element is selected from aptamers and antibodies. Embodiments of the capture moiety and methods thereof are disclosed in PCT Application Serial No. PCT/US2019/053426, incorporated herein by reference.

EXAMPLES

Example 1

Cell Preparation Protocol (CS10 Cryopreserved Cells Mixed Cell Lines)

Two cell mixture tubes are removed from liquid nitrogen (HEK293T and NIH3T3) and placed in a 37° C. water bath. After 90 sec at 37° C., the tubes are removed from the water bath and gently inverted until their entire contents are liquid. The vials are placed on wet ice and moved to a biosafety cabinet. The outside of the vials are wiped with an IPA wipe and gently inverted 5 times to mix cells.

The contents of both tubes are transferred to a 15 mL tube to which 9 mL of pre-warmed (to room temperature) DMEM+10% FBS is added slowly. The tube is gently inverted 3-5 times after adding the media. The tube is centrifuged at 150×g for 8 minutes at room temperature The supernatant is aspirated and the cell pellet resuspended using a wide-bore pipette tip in 1 mL PBS with 0.04% BSA and gently mixed 5 times and the tube inverted. The cells are then centrifuged at 150×g on a benchtop centrifuge for 5 min. The supernatant is aspirated again, using a normal bore pipette tip, 200 µL PBS with 0.04% BSA is then added and gently mixed 10-15 times until cells are completely suspended.

Using a wide bore pipette tip, 200 µL of the cell suspension is withdrawn and a tip strainer is then added onto the end of the pipette tip. The cell suspension is gently dispensed through the tip strainer into a fresh 1.5 mL tube.

Cell viability and cell concentration are via cell quantification protocol below. Cell mixture aliquots at 400 cells/µL with 50 µL volume and 80 cells/µL with 50 µL volume are then prepared.

Example 2

Cell Quantification 0.4% trypan blue stain is vortexed and centrifuged briefly. Using a wide-bore pipette tip, the strained cells are mixed 10 times. 10 µL cells are immediately aliquoted and mixed with 10 µL 0.4% trypan blue stain and then gently mixed with a wide-bore pipette tip. 10 µL of the trypan blue stained cells are transferred to a cell counting slide and cell concentration and viability is determined. The cells are then diluted to 500 cells/µl in an appropriate buffer (e.g., PP05) using a wide-bore pipette tip. Equal amounts of the cells are combined using a wide-bore pipette tip to generate a 500 cells/µL cell mixture which is then mixed and placed on ice.

Example 3

Cell Preparation Protocol (PBMCs)

A PBMC tube is removed from liquid nitrogen and placed in a 37° C. water bath. After 90 sec at 37° C., the tube is removed gently inverted until the entire contents are liquid. The vial is placed on ice and moved to place vial on wet ice and moved to a biosafety cabinet. The outside of the vial is wiped with an IPA wipe and gently inverted 5 times to mix cells.

10 µL of the contents are immediately transferred into a new tube, with the remaining sample left on ice. The above cell quantification protocol is performed to quantify viability and cell concentration The remaining vial contents are transferred to a 15 mL tube. 10 mL of pre-warmed (room temperature) DMEM+10% FBS is added to the cells (about 1 mL per second). The capped tube is gently inverted 3-5 times after adding the media. The tube is centrifuged at 200×g for 8 minutes at room temperature. The supernatant is aspirated without disturbing the pellet and the cells resuspended in 12 mL pre-warmed DMEM+10% FBS. The tube is centrifuged again at 200×g for 8 minutes at room temperature and the supernatant aspirated. The pellet is resuspended using a wide-bore pipette tip in 1 mL PBS with 0.04% BSA and gently mixed 5 times. The cells are then centrifuged at 200×g on a benchtop centrifuge for 5 min and the supernatant aspirated using a normal bore pipette tip. 1 mL PBS with 0.04% BSA is added and then gently mixed 10-15 times until cells are completely suspended.

Using a normal bore pipette tip, 1 mL of the cell suspension is aspirated and a cell strainer added onto the end of the pipette. The cell suspension is gently dispensed through the tip strainer into a fresh 1.5 mL tube. Cell quantification if performed as above and a cell mixture aliquot at 200 cells/µL with 50 µL volume is prepared.

Example 4

Sequencing Verification of Antibody-Derived Tags 5 mL of staining buffer of 2% BSA+0.01% Tween in PBS is prepared in a 1.5 mL Tube. A cryopreserved HEK/3T3 cell mixture is prepared as discussed above for cell staining. One million cells are resuspended in 100 µL of staining buffer. 10 µL FC blocking reagent is added and gently mixed 10 times with a normal bore pipette tip. The mixtures is incubated for 10 min at 4° C.

While incubation is proceeding, an antibody pool of 0.5 µg of each antibody-conjugate (0.5 µL of each 1 µg/µL antibody-conjugate) is prepared. The antibody-oligo conjugates used are 99381 CD3 (UCHT1) (Oligo Conjugate OC135CX)—/5/CCTTGGCACCCGAGAATTCCAAAT-CAATGAGTATACBAAAAAAAAAAAAAAAA AAAAAAAAAAAAAAA*A*A (SEQ ID NO: 1) and 86569 CD19 (HIB19) (Oligo Conjugate OC132CX)—/5'/CCTTGGCACCCGAGAATTCCATGCGCACCAT-GAGCTBAAAAAAAAAAAAAAAA AAAAAAAAAAAAAAA*A*A (SEQ ID NO: 2).

The antibody-conjugate pool is added to cells and incubated for 30 min at 4° C. The cells are washed 3 times with 1 mL staining buffer with each spin at 350×g for 5 min at 4° C. Cells are then resuspended in 200 μL PBS. Using a wide bore pipette tip, the 200 μL cell suspension is withdrawn and a 40 micron tip strainer is placed onto the end of the pipette The cell suspension is gently dispensed through the tip strainer into a fresh 1.5 mL tube. 0.4% trypan blue stain is vortexed and centrifuged briefly. Using a wide-bore pipette tip, the strained cells are gently mixed 10 times. 10 μL of cells and mix are immediately aliquoted with 10 μL 0.4% trypan blue stain, gently pipette mix with wide-bore pipette tip 10 μL of trypan blue stained cells are placed on a cell counting slide and cell concentration and viability is determined (viability must be >95% to proceed). The cells are diluted to 80 cells/μl in appropriate buffer in a tube using a wide-bore pipette tip.

Cells are Captured as Follows:

A 28 μL aliquot of templates is obtained in a 0.2 mL strip tube at room temp. A pre-mix of Proteinase K and DTT is made by adding 7 μL of PK+7 μL of DTT to a tube.

The cell suspension is mixed with a wide-bore tip set at 25 μL stroke, up and down 10 times. 2 μL of pre-mix is added to each tube 5 μL of 200 cells or 5 μL of 400 cell mixture individually, in that order, using a narrow bore tip for the cells. The mixture is pipetted up and down 10 times, while moving the tip throughout the mixture starting from the bottom and moving up, then returning to the bottom, with a low retention tip, 28 μL stroke.

150 μL of partitioning reagent. The hydrogels should move up through the fluid. If they don't, the bottom of the tube may be flicked to ensure hydrogels aren't stuck at the bottom. The mixture is then vortexed at maximum RPM (setting 3000 rpm for 45 sec).

The emulsion quality is visually checked after one minute. If not excellent, additional vortexing for another 15 seconds can be performed and the quality check repeated. Excellent quality refers to the homogeneity of emulsion being the same from every angle.

135 μL of oil is transferred out of each tube (P200 tip into bottom, wait 5 seconds, then aspirate) and discard. 25 μL 0.05% partitioning reagent is added on top and allowed to sink to the bottom. The mixture is incubated at 70° C. for 5 min, 55° C. for 20 min, 4° C. 30 min, lid temp 105° C. The samples are removed and proceed promptly to next step The emulsions are broken as follows: They are removed from refrigeration and warmed for 10 min at room temperature. Aliquots of 1 mL chilled 2× First Strand Buffer with 1% washing buffer are prepared in one 1.5 mL tube per sample and kept on ice. Aliquots of 2×FSB 1% F68 are prepared in separate PCR tube strips (180 uL per sample) and kept on ice. 25 μL incubation oil is removed via 2×12.5 μL (can use 8-channel pipette). The tubes are overlaid with 180 μL breaking buffer (at room temp). 40 μL departitioning buffer is added and vortexed to break emulsion (3 seconds). The tubes are centrifuged for 15 seconds on a benchtop plate spinner and stopped manually. The bottom oil phase is removed, 3×17 μL, and beads are retained in the tubes. This should remove all the oil and the tubes should be kept on ice.

The templates are washed with 2×FSB as follows: The pipette is set to 170 μL to transfer broken emulsion into 1.5 mL tube pre-filled with washing buffer. The tube is kept in a cold block. 180 μL 2×FSB 1% F68 from pre-filled PCR strip is aspirated and the original emulsion tube rinsed. The wash is combined into the 1.5 mL tube filled with broken emulsion. Each tube is pulse vortexed (2×1 sec) with a quick flick in between vortexing to ensure no templates are stuck at bottom, then spun down for 1 minute. 1.0 mL of the aqueous phase is removed without disturbing the gel beads pellet. 1 mL 2× First Strand Buffer 1% F68 is added to the templates. Each tube is pulse vortexed (2×1 sec) with a quick flick in between vortexing to ensure no templates stuck at bottom, then spun down for 30 sec.

1.0 mL of the aqueous phase is removed again without disturbing the gel beads pellet. The aqueous volume is reduced to slightly above the 100 μL line on the tube. The entire remaining beads mix is added into a new 0.2 mL PCR tube and spun down for ~30 secs on the plate spinner. A line is drawn slightly above templates—aqueous interface. The supernatant above the templates is removed to within a couple μL of the pellet without disturbing the gel beads pellet. The 0.2 mL tube is placed on a cold block until reverse transcription.

For reverse transcription, 25 μL of master mix is added to each sample and mixed. The samples are placed on a thermal cycler at 25° C. for 30 minutes, 42° C. for 90 minutes, and 85° C. for 10 minutes followed by a 4° C. hold. Whole transcriptome amplification (WTA) is then performed using WTA master mix at 95° C. for 3 minutes followed by 16 cycles of 98° C. for 15 seconds, 67° C. for 20 seconds, 68° C. for 4 minutes, and 72° C. for 5 minutes followed by a 4° C. hold.

Example 5

Purification and Analysis

Amplified cDNA is isolated from templates by size exclusion using Corning co-star 0.45 micron columns. 7×50 μL IDTE is pre-aliquoted into strip tubes. WTA-amplified samples are retrieved from 4° C. 100 μL nuclease-free water is added to the column and spun at 13,000×g for 1 minute, flow-through is discarded. ~100 μL (total) of each WTA reaction mix is added to the column. The column is centrifuged for 5 minutes at 13,000×g and the flow-through kept.

The collected flow-through is added to a PCR tube and purified with Ampure beads (0.6×) and both the antibody conjugates and the supernatant are kept. The ADT fraction is then purified with Ampure beads 2 an additional two times and transferred to PCR tubes.

The ADT sequencing library is then amplified using an ADT master mix comprising 2× Kapa HiFi Hotstart Readymix, 10 μM Small RNA RPIx primer, 10 μM P5-SMART PCR hybrid oligo, and water and added to the purified ADT fraction.

The mixture is then amplified using the following thermal cycling program:

| 95° C. | 3 min | x1 |
| 95° C. | 20 sec | x10 |
| 60° C. | 30 sec | |
| 72° C. | 20 sec | |
| 72° C. | 5 min | x1 |
| 4° C. | hold | |

The PCR amplification product is then purified using Ampure beads, quantified using fluorometric quantification, and evaluated using Bioanalyzer high-sensitivity DNA analysis (Agilent).

The WTA samples are diluted and subjected to a tagmentation protocol (Illumina Nextera). The samples are then pooled for sequencing. Sequencing data is then analyzed to verify the presence of both mRNA-derived cDNA for gene expression profiling as well as the presence of nucleic acid tags/labels from the various antibody conjugates.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

prises first capture probes comprising capture sequences and second capture probes comprising template-switching oligos (TSOs);
adding a second fluid to the first fluid;
shearing the fluids to generate a plurality of monodisperse droplets simultaneously that contain a single one of the template particles and a single one of the target cells;
amplifying and sequencing nucleic acid labels from the nucleic-acid-labelled, target-specific antibodies to identify target proteins expressed by the target cells.

2. The method of claim 1 further comprising quantifying the target proteins expressed by the target cells.

3. The method of claim 2 wherein the nucleic acid labels comprise a unique molecular identifier sequence.

4. The method of claim 2 wherein the nucleic acid labels comprise a PCR handle.

5. The method of claim 1, wherein the template particles further comprise one or more compartments.

6. The method of claim 5, wherein the one or more compartments contain a reagent selected from a group comprising a lytic reagent, a nucleic acid synthesis reagent, or combination thereof.

7. The method of claim 6 further comprising, prior to the step of amplifying and sequencing nucleic acid labels, lysing each of the single target cells contained within the monodisperse droplets to release a plurality of distinct mRNA molecules;

What is claimed is:

1. A method for single cell analysis, the method comprising:
incubating a plurality of nucleic-acid-labelled, target-specific antibodies with a plurality of target cells to promote binding of the nucleic-acid-labelled, target-specific antibodies to target proteins expressed by the target cells;
washing the incubated target cells to remove unbound nucleic-acid-labelled, target-specific antibodies;
combining template particles and the washed target cells in a first fluid, wherein each template particle com-capturing the plurality of distinct mRNA molecules with the first capture probes;
extending the first capture probes with reverse transcriptase to form nascent first strand cDNAs;
annealing the nascent first strand cDNAs to the TSOs and copying the TSOs to generate cDNAs that are bound to the template particles and contain copies of the plurality of distinct mRNA molecules and the TSOs;
breaking the droplets to release the cDNA; and
amplifying and sequencing the cDNA to quantify the plurality of distinct mRNA molecules.

8. The method of claim 7 wherein the nucleic acid labels comprise a capture portion.

9. The method of claim 8 wherein the capture portion comprises a poly A sequence.

10. The method of claim 7, further comprising generating an expression profile for each of the single target cells after quantifying the plurality of distinct mRNA molecules.

11. The method of claim 1, wherein the first fluid is an aqueous fluid.

12. The method of claim 11, wherein the second fluid comprises an oil.

13. The method of claim 12, wherein shearing the fluids comprises one of using a vortexer or pipetting.

14. The method of claim 6, wherein the nucleic acid synthesis reagent comprises a polymerase.

15. The method of claim 6, wherein the reagent is released from the one or more compartments in response to an external stimulus.

16. The method of claim 8, wherein the template particles further comprise a plurality of capture probes comprising:

a universal primer sequence;

at least one barcode; and a capture sequence that hybridizes to one or more of the plurality of distinct mRNA.

17. The method of claim 16, wherein the capture sequence is selected from one of a poly T nucleotide sequence, a gene-specific nucleotide sequence, or a random nucleotide sequence.

18. The method of claim 16, wherein the capture sequence of one or more of the capture probes hybridizes to the capture portion of one or more of the nucleic acid labels.

19. The method of claim 16, wherein mRNA attached to the template particle by the capture probes is reverse transcribed to generate a first strand comprising cDNA and the barcode sequence.

* * * * *

SEQUENCE LISTING

<160> NUMBER OF SEQ ID NOS: 2

<210> SEQ ID NO 1
<211> LENGTH: 69
<212> TYPE: DNA
<213> ORGANISM: Artificial Sequence
<220> FEATURE:
<223> OTHER INFORMATION: Synthetic sequence

<400> SEQUENCE: 1
ccttggcacc cgagaattcc aaatcaatga gtatacbaaa aaaaaaaaaa aaaaaaaaa      60 aaaaaaaaa                                                            69

<210> SEQ ID NO 2
<211> LENGTH: 69
<212> TYPE: DNA
<213> ORGANISM: Artificial Sequence
<220> FEATURE:
<223> OTHER INFORMATION: Synthetic sequence

<400> SEQUENCE: 2
ccttggcacc cgagaattcc atgcgcacca tgagctbaaa aaaaaaaaaa aaaaaaaaa      60 aaaaaaaaa                                                            69